US010399004B2

(12) United States Patent
Hoyme et al.

(10) Patent No.: US 10,399,004 B2
(45) Date of Patent: Sep. 3, 2019

(54) THERMALLY INTEGRATED DISTILLATION SYSTEMS AND PROCESSES USING THE SAME

(71) Applicant: Eastman Chemical Company, Kingsport, TN (US)

(72) Inventors: Craig Alan Hoyme, Fall Branch, TN (US); Robert Scott Huss, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 323 days.

(21) Appl. No.: 15/259,796

(22) Filed: Sep. 8, 2016

(65) Prior Publication Data

US 2018/0065061 A1    Mar. 8, 2018

(51) Int. Cl.
*B01D 3/14* (2006.01)
*B01D 3/36* (2006.01)
*C07C 209/86* (2006.01)

(52) U.S. Cl.
CPC .............. *B01D 3/143* (2013.01); *B01D 3/141* (2013.01); *B01D 3/36* (2013.01); *C07C 209/86* (2013.01)

(58) Field of Classification Search
CPC .......... B01D 3/141; B01D 3/143; B01D 3/36; C07C 209/86
See application file for complete search history.

(56) References Cited

U.S. PATENT DOCUMENTS

| 2,715,604 | A | * | 8/1955 | Weaver, Jr. | ............. C07C 29/80 203/98 |
| 3,024,170 | A | * | 3/1962 | Othmer | ................... C07C 51/46 159/DIG. 19 |

(Continued)

FOREIGN PATENT DOCUMENTS

| CN | 101367710 A | 2/2009 |
| CN | 101700916 B | 11/2011 |

(Continued)

OTHER PUBLICATIONS

Notification of Transmittal of the International Search Report and the Written Opinion of the International Searching Authority, or the Declaration dated Nov. 20, 2017 received in International Application No. PCT/US2017/049272.

(Continued)

*Primary Examiner* — Jonathan Miller
(74) *Attorney, Agent, or Firm* — Tammye L. Taylor

(57) ABSTRACT

Processes and systems for separating a mixture of three or more chemical components into multiple product streams each enriched in one of the components are provided herein. In some aspects, the present invention relates to processes for the separation of a chemical mixture including at least a heavy key component, an intermediate key component, and a light key component to form a product stream enriched in the light key component, a product stream enriched in the intermediate key component, and a product stream enriched in the heavy key component. Systems described herein may include one or more thermally coupled distillation columns including, for example, a dividing wall column, or a plurality of distillation columns arranged in a thermally integrated configuration.

15 Claims, 10 Drawing Sheets

(56) References Cited

U.S. PATENT DOCUMENTS

| | | | | |
|---|---|---|---|---|
| 3,412,016 | A * | 11/1968 | Graven | B01D 3/141 196/102 |
| 4,230,533 | A * | 10/1980 | Giroux | B01D 3/14 196/132 |
| 4,740,273 | A * | 4/1988 | Martin | C07C 41/58 203/39 |
| 5,124,004 | A * | 6/1992 | Grethlein | B01D 1/2856 202/154 |
| 5,709,780 | A * | 1/1998 | Ognisty | B01D 3/14 196/99 |
| 6,291,734 | B1 * | 9/2001 | Stork | B01D 3/141 196/111 |
| 6,514,387 | B1 | 2/2003 | Emmrich et al. | |
| 6,552,242 | B1 * | 4/2003 | Rice | B01D 3/141 208/347 |
| 7,129,387 | B2 * | 10/2006 | Reyneke | B01D 3/14 585/809 |
| 7,528,290 | B2 * | 5/2009 | Zimmermann | B01D 1/007 202/152 |

FOREIGN PATENT DOCUMENTS

| | | |
|---|---|---|
| CN | 203494195 U | 3/2014 |
| CN | 104334243 A | 2/2015 |
| EP | 2 679 573 A1 | 1/2014 |
| WO | WO 96/17665 A1 | 6/1996 |
| WO | WO 2013/083618 A1 | 6/2013 |

OTHER PUBLICATIONS

Dejanovic, I. and et al.; "Chemical Engineering and Processing: Process Intensification"; Chemical Engineering and Processing, vol. 49; 2010; pp. 559-580.

Doherty, M. F. et al.; "Distillation"; Perry's Chemical Engineer's Handbook, 7$^{th}$ Edition, Section 13; 1997; pp. 13-69 to 13-81.

Le, Quang-Khoa; "Design and simulation of dividing wall column for ternary heterogeneous distillation" Master's Thesis; Chemical Engineering, Norwegian University of Science and Technology; Jun. 2014.

Le, Quang-Khoa et al.; "Dividing wall columns for heterogeneous azeotropic distillation"; Chemical Engineering Research and Design; Mar. 2015, retrieved online Oct. 8, 2015 from http://www.researchgate.net\publication\274569875; 11 pages.

Wu, Yi Chang et al.; "Energy-Saving Dividing-Wall Column Design and Control for Heterogeneous Azeotropic Distillation Systems"; Industrial & Engineering Chemistry Research, vol. 53; 2014; pp. 1537-1552.

\* cited by examiner

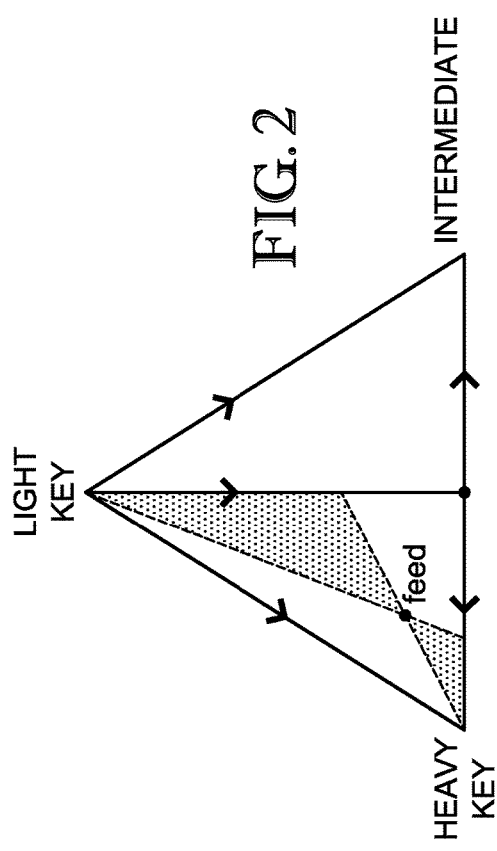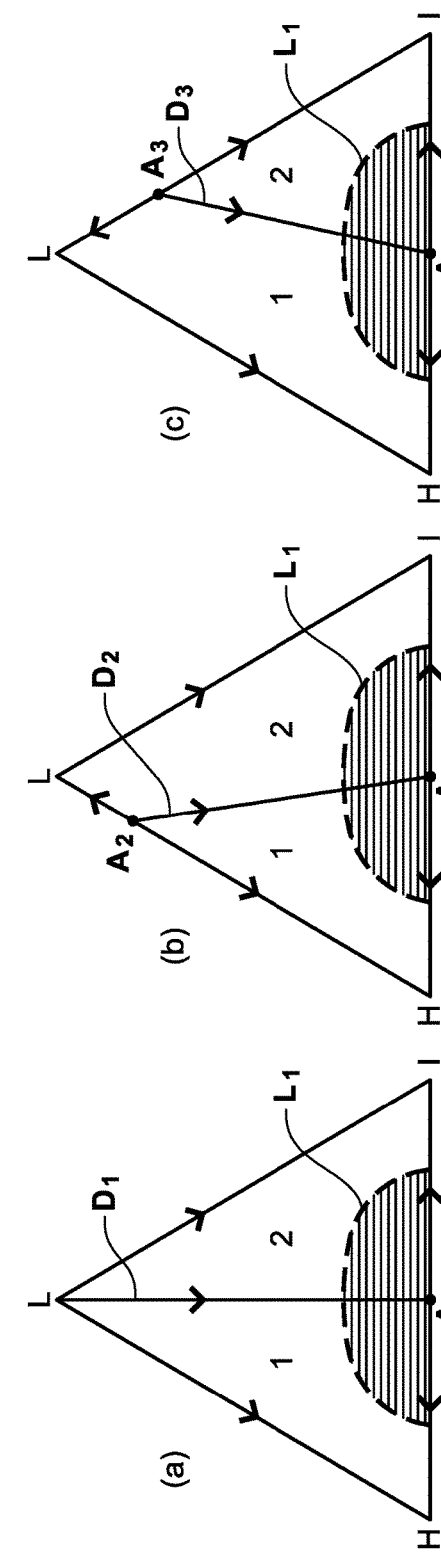
FIG. 2
FIG. 3a  FIG. 3b  FIG. 3c

THERMALLY INTEGRATED DISTILLATION SYSTEMS AND PROCESSES USING THE SAME

BACKGROUND

Field of the Invention

The present invention relates generally to processes for the separation of a mixture of three or more chemical components. In particular, this invention relates to processes and systems for separating a mixture of three or more chemical components exhibiting at least one heterogeneous azeotrope into separate product streams each enriched in one of the three components.

Description of Related Art

Separating mixtures that include three or more chemical components into multiple, purified product streams is desirable in a wide range of chemical processes and facilities. In many cases, such separations are performed using two or more distillation columns, the first of which removes the "light" (i.e., most volatile) components and the second of which separates out the "heavy" (i.e., least volatile) components from the remaining intermediate boiling components. One drawback associated with these conventional, multi-column systems for separating mixtures of three or more components is the amount of equipment required. More specifically, conventional separation systems, which include multiple columns and related equipment such as pumps, piping, valves, heat exchangers, and the like, can be very capital- and energy-intensive and expensive to operate. Furthermore, such systems have difficulty providing high purity product streams when, for example, the mixture includes one or more azeotropes.

Thus, a need exists for a distillation system capable of efficiently separating mixtures including three or more components into product streams enriched in each of the main components. Ideally, the capital and operating costs of the system would be minimized, but the product output and purity would be enhanced as compared to conventional systems. Further, such systems could be retrofitted into existing facilities, as well as being utilized in new plants, and would be usable in a wide variety of chemical processes, including those requiring at least one azeotropic separation.

SUMMARY

One embodiment of the present invention concerns a method for separating a ternary mixture comprising a light key component, a heavy key component, and at least one intermediate key component. The mixture has a distillation boundary on a distillation region diagram that intersects a heterogeneous, minimum boiling binary azeotrope between the intermediate key component and the heavy key component that has a higher boiling point than the light key component. The method comprises the steps of introducing a feed stream comprising the mixture into a thermally integrated distillation system comprising a rectification zone, a first stripping zone, a second stripping zone, and a decantation zone and withdrawing first and second overhead vapor streams from the first and the second stripping zones respectively. The method further comprises the steps of introducing the first and the second overhead vapor streams into the rectification zone, withdrawing a rectification liquid stream from the rectification zone, introducing the rectification liquid stream into the decantation zone, and separating the rectification liquid stream in the decantation zone into a first liquid phase enriched in the heavy key component and a second liquid phase enriched in the intermediate key component, wherein the first and the second liquid phases have compositions that are in different distillation regions of the distillation region diagram. The method also comprises the steps of introducing a first liquid stream comprising at least a portion of the first liquid phase into one of the first stripping zone and the second stripping zone and introducing a second liquid stream comprising at least a portion of the second liquid phase into the other of the first stripping zone and the second stripping zone. The method also comprises the steps of recovering a first bottoms product stream enriched in the heavy key component from the first stripping zone, recovering a second bottoms product stream enriched in the intermediate key component from the second stripping zone; and recovering a first overhead product stream enriched in the light key component from the rectification zone.

Another embodiment of the present invention concerns a thermally integrated distillation system for separating a ternary mixture comprising a light key component, a heavy key component, and at least one intermediate key component. The mixture has a distillation boundary on a distillation region diagram that intersects a heterogeneous, minimum boiling binary azeotrope between the intermediate key component and the heavy key component that has a higher boiling point than the light key component. The system comprises a first stripping zone configured to separate at least a portion of the mixture into a first vapor stream and a first product stream enriched in the heavy key component and a second stripping zone configured to separate at least a portion of the mixture into a second vapor stream and a second product stream enriched in the intermediate key component. The system also comprises a rectification zone configured to receive the first vapor stream and the second vapor stream and for separating the first vapor stream and the second vapor stream into a rectification liquid stream and an overhead product stream enriched in the light key component and a decantation zone configured to receive the rectification liquid stream and for separating the rectification liquid stream into a first liquid phase enriched in the heavy key component and a second liquid phase enriched in the intermediate key component, wherein each of the first and the second liquid phases have compositions that fall within different distillation regions of the distillation region diagram. The first stripping zone is configured to receive one of the first liquid phase and the second liquid phase from the decantation zone and wherein the second stripping zone is configured to receive the other of the second liquid phase and the first liquid phase from the decantation zone.

BRIEF DESCRIPTION OF THE DRAWINGS

Various embodiments of the present invention are described in detail below with reference to the attached drawing Figures, wherein:

FIG. 2 is an exemplary distillation region diagram (DRD) for a ternary mixture including a heavy key component, an intermediate key component, and a light key component that has a distillation boundary on a distillation region diagram that intersects a heterogeneous, minimum boiling binary azeotrope between the intermediate key component and the heavy key component that has a higher boiling point than the light key component;

FIG. 3a is a distillation region diagram (DRD) similar to the one shown in FIG. 2, particularly illustrating the elements of the DRD for a system characterized by DRD #004 as described in Perry's Chemical Engineer's Handbook (8$^{th}$ edition, Section 13, Doherty, M. F., et al., *Distillation*, pp. 13-69 to 13-81), particularly illustrating the distillation boundary, the liquid-liquid region, and the heterogeneous, minimum boiling azeotrope between the intermediate and heavy key components;

FIG. 3b is a distillation region diagram (DRD) similar to the one shown in FIG. 2, particularly illustrating the elements of the DRD for a system characterized by DRD #006 as described in Perry's Chemical Engineer's Handbook (8$^{th}$ edition, Section 13, Doherty, M. F., et al., *Distillation*, pp. 13-69 to 13-81), particularly illustrating the distillation boundary, the liquid-liquid region, the heterogeneous, minimum boiling azeotrope between the intermediate and heavy key components, and a homogeneous azeotrope between the light key and heavy key components;

FIG. 3c is a distillation region diagram (DRD) similar to the one shown in FIG. 2, particularly illustrating the elements of the DRD for a system characterized by DRD #009 as described in Perry's Chemical Engineer's Handbook (8$^{th}$ edition, Section 13, Doherty, M. F., et al., *Distillation*, pp. 13-69 to 13-81), particularly illustrating the distillation boundary, the liquid-liquid region, the heterogeneous, minimum boiling azeotrope between the intermediate and heavy key components, and a homogeneous azeotrope between the light key and intermediate key components;

DETAILED DESCRIPTION

Various embodiments of the present invention relate to methods and systems for separating a multicomponent mixture. More particularly, the present invention relates to methods and systems for separating a mixture comprising at least three different chemical constituents to form separate product streams, each one enriched in one of the three components, using a thermally integrated distillation system. Embodiments of the present invention may be used for mixtures that are conventionally difficult to separate, such as mixtures including at least one heterogeneous azeotrope. In some embodiments, the methods and systems described herein may be used to separate a mixture comprising a light key component, a heavy key component, and at least one intermediate key component that exhibits at least one heterogeneous minimum boiling binary azeotrope between the intermediate key component and the heavy key components that has a boiling point higher than the light key component.

Figure 1:
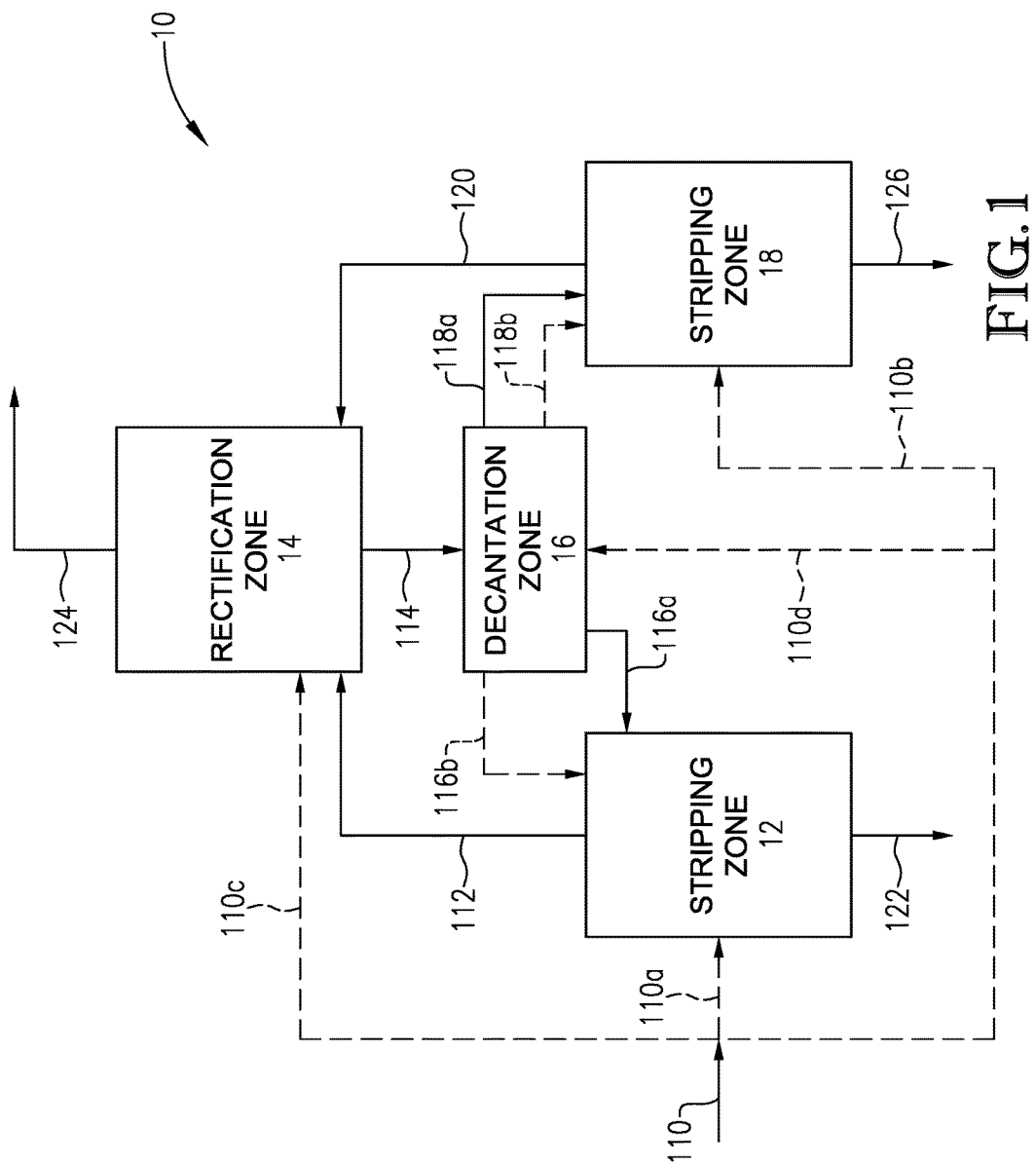
FIG. 1 is a schematic diagram of a thermally integrated distillation system according to various embodiments of the present invention, particularly illustrating the configuration of the first and second stripping zones, the rectification zone, and the decantation zone relative to one another.

Turning initially to FIG. 1, a schematic diagram of a thermally integrated distillation system 10 configured according to various embodiments of the present invention is shown. As used herein, the term "thermally integrated distillation" refers to a distillation system with at least one vapor-liquid interconnection between two or more separation zones. As shown in FIG. 1, distillation system 10 generally includes a first stripping zone 12, a rectification zone 14, a decantation zone 16, and a second stripping zone 18. In some embodiments, one or more of zones 12, 14, 16, and 18 may be present in separate process vessels, such as, for example, in two or more distillation columns, while, in other embodiments, all of the separation zones 12, 14, 16, and 18 may be present in a single process vessel, such as, for example, a dividing wall distillation column. Specific embodiments of distillation system 10 will be described in further detail below.

Distillation system 10 may be configured to separate a mixture of three or more components having different volatilities into separate product streams each enriched in one of the components. As used herein, the term "enriched," as it applies to a process stream removed from a zone, column, or other vessel, refers to the process stream that has a higher amount (by weight) of a given component than the amount (by weight) of that component present in each of the other individual stream or streams removed from the same zone, column, or vessel. For example, an overhead vapor stream withdrawn from a distillation column may be "enriched" in component A if the overhead vapor stream includes a total weight of component A that is higher than the total weight of component A present in each of the bottoms liquid stream and any side streams, on an individual basis. For example, if a feed stream including 7 pounds per hour (lb/h) of component A were divided into an overhead stream including 5 lb/h of component A and a bottoms stream including 2 pounds per hour (lb/h) of component A, the overhead stream could be said to be enriched in component A.

The amount of a given component in which a stream is enriched can be at least about 0.05, at least about 0.5, at least about 1, at least about 2, at least about 5, or at least about 10 percent higher than the amount of that component in the product stream with the next highest amount of the given component according to the following equation: (weight of component A in the enriched stream−weight of component A in the product stream having the next highest amount of component A)/(weight of component A in the product stream having the next highest amount of component A), expressed as a percentage. In some embodiments, distillation system 10 may be configured to separate a feed stream that comprises at least a light key component, a heavy key component, and at least one intermediate key component into a product stream enriched in the light key component, a product stream enriched in the intermediate key component, and a product stream enriched in the heavy key component.

As used herein, the term "light key component" refers to the least volatile component separated in the most volatile phase, and the term "heavy key component" refers to the most volatile component separated in the least volatile phase. As used herein, the term "intermediate key component," refers to a chemical component having a volatility between the light key component and the heavy key component which is predominantly separated in an intermediate volatility phase. Although generally described herein with respect to the light key component, heavy key component, and intermediate key component, it should be understood that the mixtures capable of being separated according to the present invention may further include other components, including, for example, one or more components lighter (i.e., more volatile) than the light key, one or more components heavier (i.e., less volatile) than the heavy key, and/or one or more additional intermediates having boiling point between the light key and heavy key, as long as the additional components do not change the characteristics of the distillation region diagram (DRD) used to describe the behavior of the light key component, the heavy key component, and the intermediate key component. Additional information about DRDs will be described in further detail below.

In some embodiments, the mixture separated in distillation system 10 includes at least one azeotrope. As used herein, the term "azeotrope" refers to a mixture of two or more components that have a constant boiling point and composition that cannot be separated by simple distillation. The azeotrope or azeotropes present in the mixture to be separated in distillation system 10 may comprise at least one binary azeotrope, formed between two of the mixture components. In some embodiments, the mixture may not include any ternary azeotropes, which are formed between three components of the mixture, or higher order azeotropes, which are formed between more than three components.

When used to separate a mixture including at least a light key component, a heavy key component, and at least one intermediate key component, the feed stream to distillation system 10 includes at least one binary azeotrope between the intermediate key component and the heavy key component, and may further include an azeotrope between the light key component and the intermediate key component or an azeotrope between the light key component and the heavy key component. Distillation system 10 may be configured to separate mixtures including a single azeotrope, as well as mixtures that include two or more azeotropes. In some embodiments, when the mixture includes a binary azeotrope between the intermediate key component and the heavy key component, that azeotrope has a boiling point higher than the light key component. Additional details regarding specific embodiments will be discussed below.

The mixtures suitable for separation in distillation system 10 may include at least one heterogeneous azeotrope. As used herein, the term "heterogeneous azeotrope" refers to an azeotrope in which one or more of the components is immiscible in one or more of the other components. In addition, the mixtures may further include at least one additional heterogeneous azeotrope or at least one homogeneous azeotrope. As used herein, the term "homogeneous azeotrope" refers to an azeotrope in which the components are completely, or nearly completely, miscible in one another. Homogeneous azeotropes form a single liquid phase, while heterogeneous azeotropes form two-phase mixtures. In some embodiments, the mixture separated in distillation system 10 includes at least one heterogeneous azeotrope and may further include at least one other heterogeneous azeotrope or at least one homogeneous azeotrope. In some embodiments, the mixture includes one heterogeneous azeotrope with no additional azeotropes.

Overall, the composition of a mixture including three or more components may be described according to the relative volatilities of its components, and, in particular, according to how the composition of the mixture changes as it is subjected to conditions that cause it to vaporize. A convenient method for characterizing the equilibrium behavior of such mixtures is called a Residue Curve Map (RCM). A Residue Curve Map summarizes the liquid composition over time as a given mixture is subjected to a single-stage batch distillation. When used to describe the behavior of a ternary mixture, the results are plotted as residue curves on a triangular graph and each residue curve represents the changes in a liquid composition between a given starting and ending composition. The set of residue curves for a given system collectively forms the Residue Curve Map. The fundamental structure of RCMs can be defined by Distillation Region Diagrams (DRDs) which show pure components, azeotropes, relative boiling points, and distillation boundaries.

Distillation Region Diagrams are identified by number and are described in Perry's Chemical Engineer's Handbook ($8^{th}$ edition, Section 13, Doherty, M. F., et al., *Distillation*, pp. 13-69 to 13-81), the entire disclosure of which is incorporated herein to the extent not inconsistent with the present disclosure. This reference provides a numbered list of all known DRDs for azeotropic ternary mixtures, provides a full description of how to determine which DRD classifies the equilibrium behavior of a given ternary mixture, and also provides a description of RCMs and their relation to DRDs.

Additionally, this reference describes distillation regions and the limitations of the distillation boundaries for each mixture in simple distillation systems. As used herein, the term "distillation region," refers to an isolated compositional area separated by at least one distillation boundary. A "distillation boundary" refers to a compositional curve that typically cannot be crossed with simple distillation. Because of these distillation boundaries, the potential product purities achievable by simple distillation of azeotropic multicomponent mixtures have conventionally been limited for at least one of the three components.

One example of a DRD for a ternary system in which the intermediate key component and heavy key component form a binary minimum boiling azeotrope that has a boiling point higher than the light key component is provided in FIG. 2. As shown in FIG. 2, the DRD is a triangular diagram including a light key component vertex, an intermediate key component vertex, and a heavy key component vertex. A distillation boundary extending between the light key component vertex and the azeotropic composition of intermediate and heavy key components divides the diagram into two distillation regions.

When the starting composition of a given mixture of falls within the distillation region that includes the heavy key component as the stable node, the shaded regions shown in FIG. 2 correspond to the product compositions obtainable by simple distillation. In particular, if subjected to simple distillation, the mixture illustrated by the DRD depicted in FIG. 2 would provide a product stream enriched in the heavy key component and a product stream enriched in the light key component. However, the purity of the stream including the intermediate key component would be limited by the distillation boundary and the composition of the binary azeotrope.

In some embodiments, ternary mixtures separable by processes and systems described herein may be classified by one of DRD #004, DRD #006, and DRD #009 as described in Perry's Chemical Engineer's Handbook ($7^{th}$ ed.; Chapter 13, pages 72-78). A reproduction of DRD #004, DRD #006, and DRD #009 are provided in FIGS. 3a through 3c, respectively. When the mixture separated by distillation system 10 is characterized by DRD #004, as shown in FIG. 3a, the distillation boundary ($D_1$) extends between the light key component vertex (L) and the binary azeotrope of the intermediate and heavy key component, shown as $A_1$ in FIG. 3a. The distillation boundary $D_1$ divides the diagram into first and second distillation regions, labeled as 1 and 2, respectively, in FIG. 3a. If the intermediate-heavy key component binary azeotrope, shown as $A_1$ in FIG. 3a, is heterogeneous, the DRD #004 diagram also includes a liquid-liquid region, $L_1$, that extends into distillation regions 1 and 2, as shown in FIG. 3a.

In some embodiments, the mixture separated by distillation system 10 may further include a minimum boiling azeotrope between the light key component and the heavy key component, or a minimum boiling azeotrope between the light key component and the intermediate key component. Such systems may respectively be characterized by DRD #006 and DRD #009, examples of which are depicted in FIGS. 3b and 3c, respectively. As shown in FIG. 3b, ternary mixtures characterized by DRD #006 further comprise a minimum boiling binary azeotrope between the light key component and the heavy key component, shown as point $A_2$ in FIG. 3b, and the distillation boundary $D_2$ of this DRD extends from the light key component/heavy key component azeotrope $A_2$ to the intermediate key component/heavy key component azeotrope $A_1$.

Similarly, ternary mixtures characterized by DRD #009 further include a minimum boiling binary azeotrope between the light key component and the intermediate key component, shown as point $A_3$ in FIG. 3c, and the distillation boundary $D_3$ of DRD #009 extends from the light key component/intermediate key component azeotrope $A_3$ to the intermediate key component/heavy key component azeotrope $A_1$. As show by liquid-liquid region $L_1$ in each of FIGS. 3b and 3c, the intermediate key component/heavy key component azeotrope $A_1$ is a heterogeneous azeotrope. In some embodiments, the light key component/heavy key component azeotrope $A_2$ and/or the light key component/intermediate key component azeotrope $A_3$ may also be heterogeneous, which would result in a separate or a single liquid-liquid region (not shown) encompassing one or both of those azeotropes. In some embodiments, as shown in FIGS. 3b and 3c, the light key component/heavy key component azeotrope $A_2$ and the light key component/intermediate key component azeotrope $A_3$ may also be homogeneous.

Although generally described herein with respect to the light key component, heavy key component, and intermediate key component, it should be understood that the mixtures capable of being separated according to embodiments of the present invention may further include other components, including, for example, one or more components lighter than the light key, one or more components heavier than the heavy key, and/or one or more additional intermediates having boiling point between the light key and heavy key. The behavior of such mixtures including components in addition to the light key component, heavy key component, and intermediate key component may be characterized according to at least one of the DRDs as described above, as long as the additional components do not alter the characteristics of the DRD.

Referring again to FIG. 1, a feed stream in line 110 comprising a ternary mixture as described above may be introduced into one or more separation zones of distillation system 10. For example, in some embodiments, the feed stream may be introduced into first stripping zone 12 as shown by dashed line 110a, while in other embodiments, the feed stream may be introduced into the second stripping zone 18 via line 110b. Additionally, or in the alternative, the feed stream may be introduced into rectification zone 14 as shown by line 110c, or it may be introduced into decantation zone 16, as shown in line 110d. When introduced into decantation zone 16, it may be introduced directly into the decantation zone as shown in FIG. 1, or it may be combined with a portion of the rectification liquid introduced into decantation zone 16 via line 114 (embodiment not shown in FIG. 1). Systems configured according to embodiments of the present invention may permit the feed may be introduced into more than one location (with the option of changing the feed location during operation), or may only be configured with one of the feed locations described above.

The specific location, or locations, where the feed stream is introduced may depend on a number of factors and, in some embodiments, may depend on the composition of the feed. For example, when the feed stream includes a higher concentration or larger amount of the heavy key component as compared to the light key component and intermediate key component, the feed may be introduced into first stripping zone 12 via line 110a. When plotted on a DRD, such compositions would be located in the distillation region containing the heavy key component vertex (H), an example of which is shown as distillation region 1 in FIGS. 3a through 3c.

When the feed includes a higher concentration or larger amount of the intermediate key component as compared to the heavy key component and light key component, the feed may be introduced into second stripping zone 18 via line 110b. Such compositions would be located in the distillation region including the intermediate key component vertex (I), an example of which is shown by distillation region 2 in FIGS. 3a through 3c. When the feed stream includes a higher concentration or larger amount of the light key component as compared to the heavy key component and the intermediate key component, it may be introduced into the rectification zone 14, as shown by line 110c. Such compositions could be present in the distillation region including the light vertex L, which may be in distillation regions 1 and/or 2, depending on which DRD best describes the ternary mixture being separated. When the feed stream includes a two-phase liquid mixture, it may be introduced into decantation zone 16 via line 110d. When plotted on a DRD, such compositions lie within the liquid-liquid region $L_1$, examples of which are shown in FIGS. 3a through 3c.

Referring back to FIG. 1, in some embodiments, a stream in line 110a, which may include all or a portion of a ternary mixture as described above, may be introduced into a first stripping zone 12, wherein it can be separated into a first vapor stream in line 112 and a first liquid stream in line 122. As used herein, the terms "first," "second," "third," and the like are used to describe various elements, but such elements should not be unnecessarily limited by these terms. These terms are only used to distinguish one element from another and do not necessarily imply a specific order or even a specific element. For example, an element may be regarded as a "first" element in the description and a "second"

element in the claims without being inconsistent. Consistency is maintained within the description and for each independent claims, but such nomenclature is not necessarily intended to be consistent therebetween.

As shown in FIG. 1, the first vapor stream in line 112 may be introduced into rectification zone 14 along with a second vapor stream in line 120 withdrawn from second stripping zone 18. Upon introduction into rectification zone 14, the first and second vapor streams in respective lines 112 and 120 may be separated to thereby provide an overhead vapor stream in line 124 and a rectification liquid stream in line 114. In some embodiments, the overhead vapor stream in line 124 may be enriched in the light key component as compared to the feed stream in line 110, and can include, for example, at least about 35, at least about 40, at least about 45, at least about 50, at least about 55, at least about 60, at least about 70, at least about 75, at least about 80, at least about 85, or at least about 90 percent of the total amount of the light component introduced into distillation system 10 in the feed stream in line 110. In some embodiments, the overhead vapor stream in line 124 may comprise an azeotrope of the light key component and the heavy key component or it may comprise an azeotrope of the light key component and the intermediate key component, depending on the vapor-liquid physical properties of the feed stream in line 110.

Depending, at least in part, on the specific composition of the feed stream, the overhead vapor stream in line 124 can include at least about 20, at least about 30, at least about 40, at least about 50, at least about 60, at least about 70, at least about 80, or at least about 90 weight percent of the light key component, based on the total weight of the stream. In some embodiments, the stream in line 124 can include at least about 50, at least about 60, at least about 70, at least about 80, at least about 90, or at least about 95 weight percent of the light key components and components lighter (i.e., more volatile) than the light key component, based on the total weight of the stream in line 124.

As shown in FIG. 1, a rectification liquid stream may be withdrawn from rectification zone 14 in line 114. In some embodiments, the rectification liquid stream may include a higher concentration or larger amount of the intermediate and heavy key components, as compared to the light key component. For example, the composition of the rectification liquid stream in line 114 may be within the liquid-liquid region, $L_1$, of the DRD, examples of which are provided in FIGS. 3a through 3c.

As shown in FIG. 1, the rectification liquid stream in line 114 may be introduced into a decantation zone 16, wherein it can be phase separated to form a first liquid phase, enriched in the heavy key component, and a second liquid phase, enriched in the intermediate key component. The second liquid phase may have a higher concentration or a larger amount of the intermediate key component as compared to the heavy key component, while the first liquid phase may have a higher concentration or a larger amount of the heavy key component as compared to the intermediate key component. In some embodiments, the first liquid phase may have a higher density than the second liquid phase, while in other embodiments, the second liquid phase may have a higher density than the first liquid phase. When plotted on a DRD, the compositions of each of the second liquid phase and first liquid phase may fall on different sides of the distillation boundary within the liquid-liquid zone. For example, the first liquid phase may include a higher concentration or larger amount of the high boiling node in the distillation region that includes the feed, while the second liquid phase may include a lower concentration or smaller amount of the high boiling node in the region of the DRD that includes the feed.

In some embodiments, as shown in FIG. 1, a liquid stream comprising at least a portion of the first liquid phase from decantation zone 16 in line 116a can be introduced into first stripping zone 12, while a liquid stream comprising at least a portion of the second liquid phase from decantation zone 16 in line 118a can be introduced into second stripping zone 18. In other embodiments shown by the dashed lines 116b and 118b, the liquid stream comprising at least a portion of the first liquid phase from decantation zone 16 in line 118b can be introduced into second stripping zone 18, while the liquid stream comprising at least a portion of the second liquid phase from decantation zone 16 in line 116b may be introduced into first stripping zone 12.

According to some embodiments, distillation system 10 may be configured to change the stripping zone into which each of the first and second liquid phases are routed so that, for example, first stripping zone 12 may be configured to selectively receive one of the first and second liquid phases via lines 116a or 116b, and the second stripping zone 18 may be selectively configured to receive the other of the first and second phases from decantation zone 16 via lines 118b or 118a, respectively. In other embodiments, first stripping zone 12 may only be configured to receive the first liquid phase from decantation zone 16 via line 116a and second stripping zone 18 may only be configured to receive the second liquid phase from decantation zone 16 in line 118a, but the composition of the first and second product streams withdrawn from first stripping zone 12 and second stripping zone 18 via respective lines 122 and 126 may change depending on the composition of and location or locations into which the feed stream is introduced into distillation system 10. For example, according to some embodiments, the first product stream in line 122 may be enriched in one of the heavy key component and the intermediate key component, while the second product stream in line 126 may be enriched in the other of the heavy key component and the intermediate key component.

In some embodiments, the first product stream withdrawn from first stripping zone 12 via line 122 may have a higher concentration or comprise larger amount of the heavy key component, while the second product stream withdrawn from second stripping zone 18 via line 126 may have a higher concentration or comprise a larger amount of the intermediate key component. The overhead product stream withdrawn from rectification zone 14 via line 124 may have a higher concentration or comprise a larger amount of the light key component as compared to any residual intermediate key component or heavy key component, if present. In the case that the feed stream originally introduced into distillation system 10 includes additional light, heavy, and/or intermediate components, such components, or a majority of such components, may be present in the first product stream in line 122, the second product stream in line 126, or the overhead product stream in line 124, depending on the volatility of such components under the conditions of the separation.

As discussed above, in some embodiments, each of first stripping zone 12, rectification zone 14, second stripping zone 18, and, optionally, decantation zone 16 of distillation system 10 may be located in a single process vessel such as, for example, a dividing wall distillation column. Specific examples of dividing wall distillation columns configured according to several embodiments of the present invention are provided in FIGS. 4 and 5.

Figure 4:
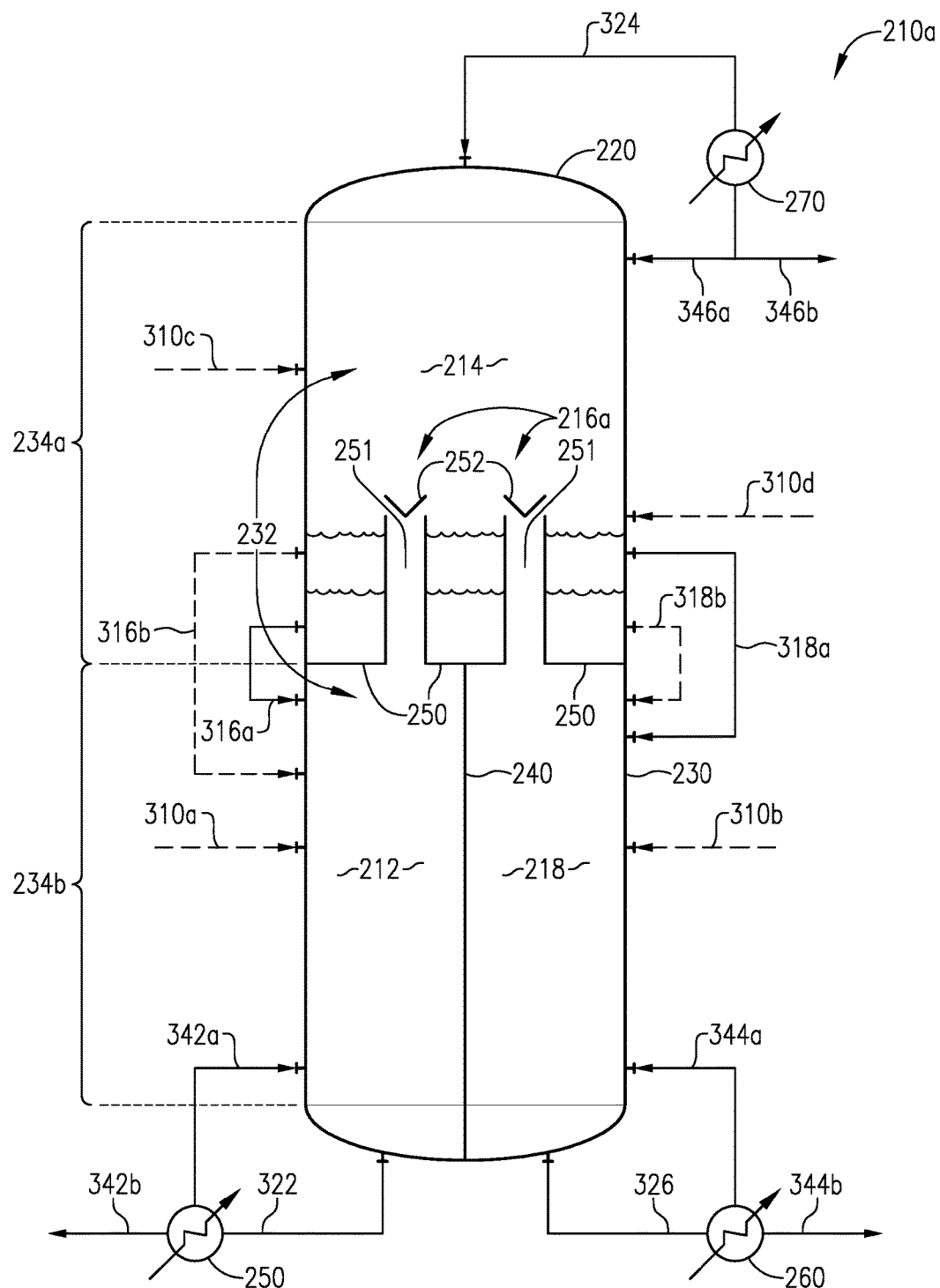
FIG. 4 is a schematic diagram of a thermally integrated distillation system configured according to embodiments of the present invention, particularly illustrating an embodiment including a dividing wall distillation column with an internal decantation zone.
Figure 5:
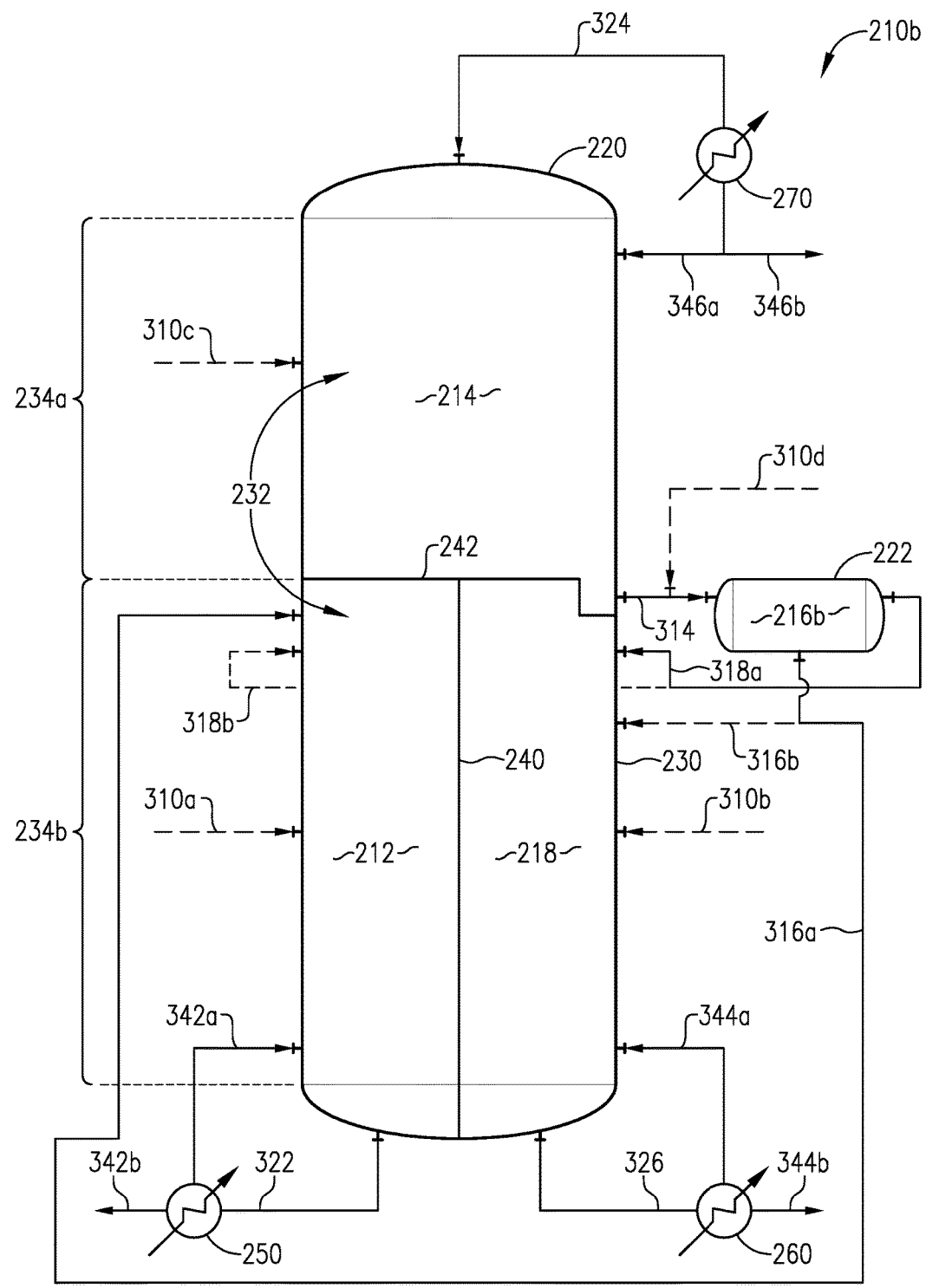
FIG. 5 is a schematic diagram of a thermally integrated distillation system configured according to embodiments of the present invention, particularly illustrating an embodiment including a dividing wall distillation column with an external decantation zone.

Turning now to FIGS. 4 and 5, distillation systems 210a and 210b suitable for performing a separation of ternary mixture according to various embodiments of the present invention are illustrated as generally including a dividing wall distillation column 220. Distillation system 210a includes an internal decantation zone 216a, while distillation system 210b includes an external decantation zone 216b defined within a decanter 222.

Turning initially to both FIGS. 4 and 5, dividing wall distillation column 220 includes a vessel shell 230 that defines an internal volume 232 having an upper portion 234a and a lower portion 234b. As shown in FIGS. 4 and 5, the upper portion 234a of internal volume 232 includes the rectification zone 214, while the lower portion 234b of internal volume 232 includes the first stripping zone 212 and the second stripping zone 218. Additionally, as shown in the embodiment depicted in FIG. 4, the internal decantation zone 216a may also be located in the upper portion 234a of internal volume 232 of dividing wall distillation column 220. Dividing wall distillation column 220 may include any suitable type of internal contacting structures (not shown) suitable for facilitating mass and energy transfer between the vapor and liquid phases. Such structures may be present in one or more of each of first stripping zone 212, second stripping zone 218, and rectification zone 214. Examples of suitable internal contacting structures for use in one or more of first stripping zone 212, second stripping zone 218, and rectification zone 214 can include, but are not limited to, random packing, structured packing, vapor-liquid contacting trays, and combinations thereof. In some embodiments, each of first stripping zone 212, second stripping zone 218, and rectification zone 214 may include internal contacting structures, while decanter 222 may be substantially empty or it may contain internal structures for facilitating liquid-liquid separation, such as, for example, baffles or screens.

As shown in FIGS. 4 and 5, each of first stripping zone 212, rectification zone 214, and second stripping zone 218 are defined within—dividing wall distillation column 220. In some embodiments, an example of which is shown in FIG. 4, decantation zone 216a can be located within the internal volume 232 of dividing wall distillation column 220, while, in another embodiments, an example of which is illustrated in FIG. 5, decantation zone 216b may be positioned outside of the internal volume 232 of dividing wall distillation column 220, in, for example, an external decanter 222. When decantation zone 216a is located within the internal volume of dividing wall distillation column 220, it may include any suitable device capable of retaining the liquid phase from rectification zone 214 and permitting the retained liquid to separate into first and second liquid phases. In some embodiments, an example of which is illustrated in FIG. 4, the internal decantation zone can include a plurality of liquid collectors 250, a plurality of chimneys or gas risers 251 to permit vapor to rise upwardly into the rectification zone 214, and a plurality of hats or caps 252 to help prevent liquid exiting rectification zone 214 from bypassing decantation zone 216a. Although described with respect to liquid collectors 250, chimneys 251, and hats 252, other structures performing a similar function are also suitable for use in decantation zone 216a.

The feed stream separated by dividing wall distillation column 220 may be introduced into one or more different locations of the column. For example, in some embodiments, all or a portion of the feed stream may be introduced into first stripping zone 212, as shown by dashed line 310a in FIGS. 4 and 5, while in other embodiments, all or a portion of the feed stream may be introduced into the second stripping zone 218, as shown by line 310b. In some embodiments, the feed stream may be introduced into rectification zone 214 as shown by line 310c, or it may be introduced into decantation zone 216a or 216b, as shown by line 310d. When introduced into an external decantation zone 216b as shown in FIG. 5, it may be introduced directly into decanter 222 (not shown), or it may be combined via line 314 with a portion of the rectification liquid introduced into decanter 222, as shown in FIG. 5.

In some embodiments, the specific location or locations into which the feed is introduced into dividing wall distillation column 220 may depend, at least in part, on the composition of the feed stream. In some embodiments, dividing wall distillation column 220 may include a feed inlet into one or more of first stripping zone 212, rectification zone 214, and second stripping zone 218, while, in other embodiments, it may include a single feed inlet into only one of these zones. When the feed is introduced into an internal decantation zone, such as decantation zone 216a shown in FIG. 4, distillation column 220 may include feed inlet into that zone. When the feed is introduced into an external decantation zone, shown as decantation zone 216b in FIG. 5, decanter 222 may or may not include a separate feed inlet in addition to the one or more fluid inlets for introducing a rectification liquid stream withdrawn from dividing wall distillation column 220 into decanter 222 as shown in FIG. 5.

Additionally, as shown in FIGS. 4 and 5, dividing wall distillation column 220 may also include a dividing wall 240 positioned within the lower portion 234b of internal volume 232. As shown in FIGS. 4 and 5, the dividing wall 240 can be configured for separating first stripping zone 212 and second stripping zone 218 and, in some embodiments, may extend to and be in contact with the lower portion of vessel shell 230 so that first stripping zone 212 and second stripping zone 218 are fluidly isolated from one another, at least along the bottom portion, by dividing wall 240.

In some embodiments when, for example, the decantation zone is located inside the internal volume of dividing wall distillation column 220, as shown by decantation zone 216a in FIG. 4, liquid collected in liquid collectors 250 may be permitted to separate into a first liquid phase and a second liquid phase within the troughs. The first liquid phase, which may be enriched in the heavy key component, may be withdrawn from the liquid collectors via line 316a and introduced into first stripping zone 212 as shown in FIG. 4, while the second liquid phase, which may be enriched in the intermediate key component, may be withdrawn from liquid collectors 250 and introduced into second stripping zone 218 via line 318a. Alternatively, the first liquid phase may be withdrawn from liquid collectors 250 and introduced into second stripping zone 218 via line 318b, while the second liquid phase withdrawn from liquid collectors 250 may be introduced into first stripping zone 212 via line 316b.

In some embodiments when, for example, the decantation zone is located outside of the internal volume of dividing wall distillation column 220, as shown by decantation zone 216b in FIG. 5, dividing wall distillation column 220 may also include a liquid draw tray or trays 242, such as, for example, a chimney tray, for separating the upper and lower portions 234a, 234b of internal volume 232 of the column 220. When the liquid draw tray 242 is a total liquid draw tray, no, or substantially no, liquid from rectification zone 214 may be directly introduced into first stripping zone 212 or second stripping zone 218 from rectification zone 214. Instead, as shown in FIG. 5, all of the rectification liquid collected in liquid draw tray 242 may be withdrawn from a liquid outlet of distillation column 220 and can be introduced into an inlet of decanter 222 via line 314.

As shown in FIG. 5, once in decanter 222, the rectification liquid stream may be separated into a second liquid phase enriched in the intermediate key component and a first liquid phase enriched in the heavy key component. In some embodiments, the second liquid phase withdrawn from decanter 222 may be introduced into one of second stripping zone 218 and first stripping zone 212 via lines 318a and 318b, respectively, while the first liquid phase from the decanter 222 can be introduced into the other of first stripping zone 212 and second stripping zone 218 via a second outlet in line 316a or 316b, respectively.

As shown in FIGS. 4 and 5, a first bottoms stream may be withdrawn from first stripping zone 212 in line 322 and heated in a first reboiler 250. A portion of the resulting heated stream may be returned to the lower portion of first stripping zone 212 via line 342a. The remaining stream in line 342b may be withdrawn from first reboiler 250 as a first product stream enriched in one of the heavy key component and the intermediate key component depending, at least in part, on the composition of the feed stream in one or more of lines 310a, 310b, 310c, and 310d. In some embodiments, the product stream in line 342b withdrawn from first stripping zone 212 can include at least about 50, at least about 60, at least about 70, at least about 75, at least about 80, at least about 85, at least about 90, at least about 95, or at least about 97 weight percent of the total amount of heavy key component or intermediate key component introduced into dividing wall distillation column 220 in the feed stream or streams in lines 310a, 310b, 310c, and/or 310d. In some embodiments, the first product stream withdrawn from first stripping zone 212 may be enriched in the heavy key component.

Similarly, a second bottoms stream may be withdrawn from second stripping zone 218 in line 326 and heated in a second reboiler 260. A portion of the resulted heated stream may be returned to the lower portion of second stripping zone 218 via line 344a. The remaining stream in line 344b may be withdrawn from second reboiler 260 as a second product stream enriched in the intermediate key component or the heavy key component, depending on the composition of the feed stream in one or more of lines 310a, 310b, 310c, and 310d. In some embodiments, the product stream withdrawn from second stripping zone 218 in line 344b can include at least about 50, at least about 60, at least about 70, at least about 75, at least about 80, at least about 85, at least about 90, at least about 95, or at least about 97 weight percent of the total amount of intermediate key component or heavy key component introduced into dividing wall distillation column 220 in the feed stream or streams in lines 310a, 310b, 310c, and/or 310d.

The overhead vapor stream withdrawn from rectifying zone 214 in dividing wall distillation column 220 via line 324 may be enriched in the light key component. As shown in FIGS. 4 and 5, the overhead vapor stream in line 324 may be cooled and at least partially condensed in a condenser 270 and the resulting liquid stream may be divided into two portions each having similar compositions. The first portion in line 346a may be reintroduced as a reflux stream into rectifying zone 214 within dividing wall distillation column 220, while the second portion in line 346b may be recovered as a third product stream enriched in the light key component. In some embodiments, the product stream in line 346b withdrawn from rectification zone 214 can include at least about 50, at least about 60, at least about 70, at least about 75, at least about 80, at least about 85, at least about 90, at least about 95, or at least about 97 weight percent of the total amount of light key component introduced into dividing wall distillation column 220 in the feed stream or streams in lines 310a, 310b, 310c, and/or 310d.

Figure 6:
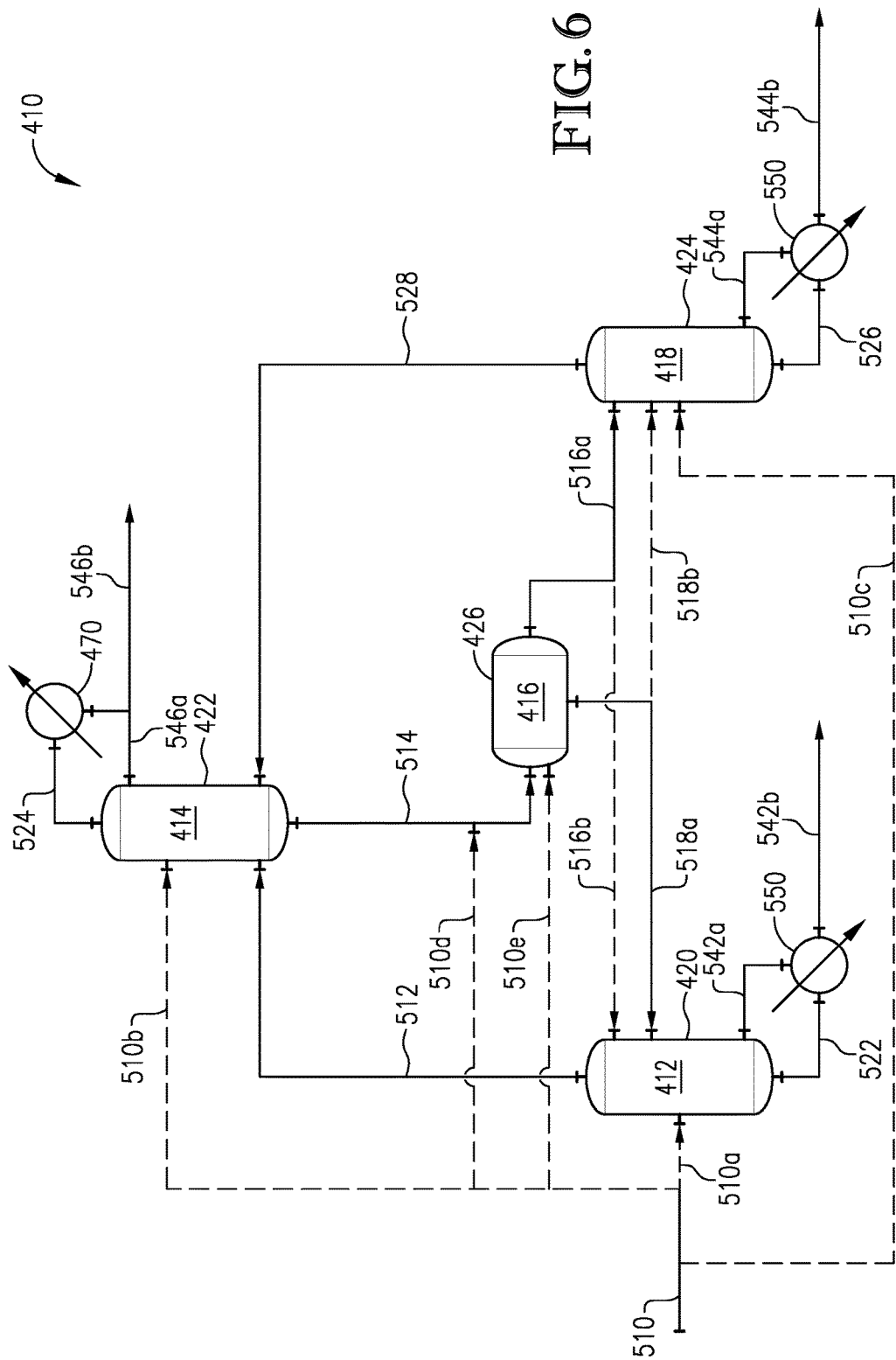
FIG. 6 is a schematic diagram of a thermally integrated distillation system configured according to embodiments of the present invention, particularly illustrating an embodiment including several separate distillation columns.

Turning now to FIG. 6, another embodiment of a distillation system 410 for separating a ternary mixture according to various embodiments of the present invention is illustrated as generally including a first distillation column 420, a second distillation column 422, a third distillation column 424, and a decanter 426. Each of first stripping zone 412, rectification zone 414, second stripping zone 418, and decantation zone 416 are defined within first distillation column 420, second distillation column 422, third distillation column 424, and decanter 426, respectively. Distillation system 410 may be configured and operated in a similar manner as distillation system 10 described with respect to FIG. 1, but includes separate vessels 420, 422, 424, and 426 for each zone 412, 414, 418, and 416, respectively. As shown in FIG. 6, decanter 426 may be located outside the internal volumes of each of first, second, and third distillation columns 420, 422, and 424.

Each of separation vessels 420, 422, 424, and 426 can be any suitable type of vapor-liquid separation vessel, and each of vessels 420, 422, 424, and 426 may be similar, or one or more may be different from one or more of the others. Each vessel 420, 422, 424, and 426 can include any suitable type of internal contacting structures (not shown) for facilitating mass and energy transfer between the vapor and liquid phases or separate liquid phases within vessels 420, 422, 424, and 426. Examples of suitable internal contacting structures can include, but are not limited to, random packing, structured packing, vapor-liquid contacting trays, baffles, screens, and combinations thereof. The internal contacting structure or structures within one vessel 420, 422, 424, and/or 426 may be the same as, or different than, the internal contacting structure or structures within one or more other vessels 420, 422, 424, and/or 426. In some embodiments, each of vessels 420, 422, and 424 may include internal contacting structures, while decanter 426 may be substantially empty or may contain baffles or screens.

As shown in FIG. 6, a feed stream that comprises a mixture including at least a heavy key component, an intermediate key component, and a light key component as described herein can be introduced into first distillation column 420 via line 510. In a similar manner as described with respect to FIGS. 1, 4, and 5, the feed stream may be introduced into a single feed location within distillation system 410, or it may be introduced into one or more different locations depending, at least in part, on its composition. For example, in some embodiments, all or a portion of the feed stream may be introduced into first distillation column 420, as shown by dashed line 510a, while in other embodiments, all or a portion of the feed stream may be introduced into the second distillation column 422, as shown by line 510b. Additionally, or in the alternative, the feed stream may be introduced into third distillation column 424 as shown by line 510c, or it may be introduced into decanter 426, as shown in lines 510d and 510e. When introduced into decanter 426, the feed stream may be introduced directly into decanter 426 as shown by line 510e, or it may be combined with a portion of the rectification liquid in line 514 via line 510d and the combined stream can be introduced into decanter 426 via line 514.

As shown in FIG. 6, first distillation column 420 separates the feed or a portion thereof into an overhead vapor stream in line 512 and a first bottoms stream in line 522 enriched in one of the heavy key component and the intermediate key component. As shown in FIG. 6, the first bottoms stream in line 522 may be withdrawn from the lower portion of first distillation column 420 and passed through a reboiler 550. A portion of the heated stream in line 542a may be returned to a lower portion of first distillation column 420, while the remaining portion of the stream in line 542b may be recovered as a first product stream enriched in the heavy key component or the intermediate key component, depending, at least in part, on the composition of the feed.

The overhead stream withdrawn from first distillation column 420 via line 512 and the overhead stream withdrawn from third distillation column 424 in line 528 may be introduced into second distillation column 422, wherein the streams may be separated into a second overhead stream enriched in the light key component in line 524 and a second bottoms stream in line 514. As shown in FIG. 6, the second overhead stream in line 524 may be cooled and at least partially condensed in condenser 470 and the resulting cooled stream may be divided into a first portion in line 546a and a second portion in line 546b. The first portion in line 546a may be reintroduced as reflux into second distillation column 422, while the second portion in line 546b may be recovered as a second product stream enriched in the light key component.

The second bottoms stream withdrawn from second distillation column 422 in line 514 may be introduced into decanter 426, wherein it can be separated into a first liquid phase enriched in the heavy key component and a second liquid phase enriched in the intermediate key component. As shown in FIG. 6, a stream including at least a portion of the second liquid phase may be withdrawn from decanter 426 and introduced into the upper portion of third distillation column 424 via line 516a or into the upper portion of first distillation column 420 via line 516b. Similarly, a stream including at least a portion of the first liquid phase may be withdrawn from decanter 426 and introduced into the upper portion of first distillation column 420 via line 518a, or into the upper portion of third distillation column 424 via line 518b. As shown in FIG. 6, the bottoms liquid stream withdrawn from third distillation column 424 in line 526 may be heated in reboiler 550 and a portion of the heated stream in line 544a may be returned to the lower portion of third distillation column 424. The other portion of the heated stream in line 544b may be recovered as a third product stream enriched in one of the intermediate key component and the heavy key component. In some embodiments, the stream in line 544b may be enriched in the intermediate key component.

Processes and systems described herein may be suitable for separating a wide variety of different chemical mixtures. In some embodiments, the ternary mixtures separable by processes and systems described herein may be classified by, for example, one of DRD #004, DRD #006, and DRD #009, as described above. The amount of each of the light key component, the heavy key component, and the intermediate key component may vary depending on the composition of the mixture, but each of the light key component, the heavy key component, and the intermediate key component can be present in an amount of at least about 0.5, at least about 1, at least about 1.5, at least about 2, at least about 2.5, at least about 5, at least about 10, or at least about 15 weight percent, based on the total weight of the mixture. In addition, or the alternative, the amount of one or more of the light key component, the heavy key component, or the intermediate key component can be not more than about 99, not more than about 95, not more than about 90, not more than about 85, not more than about 80, not more than about 75, not more than about 70, not more than about 65, not more than about 50, not more than about 45, not more than about 40, not more than about 35, not more than about 30, not more than about 25, not more than about 20, not more than about 15, or not more than about 10 weight percent, based on the total weight of the mixture.

When the mixture includes one or more additional components in addition to the light key component, the heavy key component, and the intermediate key component, such components may be present in an amount of at least about 0.5, at least about 1, at least about 2, at least about 5, at least about 10, at least about 15 weight percent and/or not more than about 30, not more than about 25, not more than about 20, not more than about 15, not more than about 10, not more than about 5, not more than about 2, or not more than about 1 weight percent, based on the total weight of the mixture. In some embodiments, the mixture may include water as one of the light key component, the heavy key component, or intermediate key component, and the remaining components can comprise organic compounds selected from the group consisting of alcohols, ketones, amines, aldehydes, paraffins, olefins, aromatic hydrocarbons, and esters. Such organic compounds can be aromatic or aliphatic and may originate from any source or process including, for example, biological processes such as fermentation, as well as a variety of others. When the mixture includes acetone, water, and at least one ketone, the ketone may comprise a ketone having at least 4 carbon atoms per molecule. Examples of such ketones can include, but are not limited to, methyl ethyl ketone, methyl isobutyl ketone, 3-pentanone, methyl isopropyl ketone, 2-pentanone, methyl n-amyl ketone, methyl isoamyl ketone, and diisobutyl ketone.

Some examples of mixtures suitable for separation by the processes and systems described herein can include, but are not limited to, one or more of the following: (i) n-butylamine/water/n-butanol/dibutylamine/tributylamine; (ii) n-butyraldehyde/water/2-ethylhexenal; (iii) n-propionaldehyde/water/2-methylpentenal; (iv) n-propionaldehyde/n-butyraldehyde/water; (v) acetone/water/n-butanol; (vi) acetone/ethanol/water/n-butanol; (vii) methanol/methacrolein/water; (viii) methanol/water/methyl methacrylate; (ix) acetone/water/ketone; and (x) methanol/water/xylene/dimethyterephthalate. Several examples of specific compositions for mixtures suitable for separation by the processes and systems described herein are summarized in Table 1, below.

TABLE 1

Examples of Ternary Mixtures for Separation by Inventive Processes & Systems

| Other Component(s) | Light Key Component | Intermediate Key Component | Heavy Key Component | Azeotrope 1 | Azeotrope 2 | DRD# |
|---|---|---|---|---|---|---|
| — | Acetone | Water | 3-Pentanone | Water/3-Pentanone | — | 004 |
| — | Acetone | Water | MPK | Water/MPK | — | 004 |
| — | Acetone | Water | MIBK | Water/MIBK | — | 004 |

TABLE 1-continued

Examples of Ternary Mixtures for Separation by Inventive Processes & Systems

| Other Component(s) | Light Key Component | Intermediate Key Component | Heavy Key Component | Azeotrope 1 | Azeotrope 2 | DRD# |
|---|---|---|---|---|---|---|
| — | Acetone | Water | MAK | Water/MAK | — | 004 |
| — | Acetone | Water | MIAK | Water/MIAK | — | 004 |
| — | Acetone | Water | C11 Ketones | Water/C11 Ketones | — | 004 |
| — | Acetone | MEK | Water | MEK/Water | — | 004 |
| — | Acetone | MIPK | Water | MIPK/Water | — | 004 |
| Acetone | Ethanol | Water | 3-Pentanone | Ethanol/Water | Water/3-Pentanone | 009 |
| Acetone | Ethanol | Water | MPK | Ethanol/Water | Water/MPK | 009 |
| Acetone | Ethanol | Water | MIBK | Ethanol/Water | Water/MIBK | 009 |
| Acetone | Ethanol | Water | MAK | Ethanol/Water | Water/MAK | 009 |
| Acetone | Ethanol | Water | MIAK | Ethanol/Water | Water/MIAK | 009 |
| Acetone | Ethanol | Water | C11 Ketones | Ethanol/Water | Water/C11 Ketones | 009 |
| Acetone | Ethanol | MEK | Water | Ethanol/Water | MEK/Water | 006 |
| Acetone | Ethanol | MIPK | Water | Ethanol/Water | MIPK/Water | 006 |
| — | Methanol | Water | DMT/pX | Water/PX, Water/DMT | — | 004 |
| — | Propionaldehyde | n-Butyraldehyde | Water | Propionaldehyde/Water | n-Butyraldehyde/Water | 006 |
| — | Propionaldehyde | i-Butyraldehyde | Water | Propionaldehyde/Water | i-Butyraldehyde/Water | 006 |
| — | n-Butyraldehyde | Water | 2-ethylhexenal | n-Butyraldehyde/Water | Water/2-Ethylhexenal | 009 |
| — | n-Butyraldehyde | Water | $C_6$ Aldols | n-Butyraldehyde/Water | Water/$C_6$ Aldols | 009 |
| — | Methanol | i-Butyraldehyde | Water | i-Butyraldehyde/Water | — | 004 |
| — | Acetone | Water | n-Butanol | Water/n-Butanol | — | 004 |
| — | Acetone | Water | i-Butanol | Water/i-Butanol | — | 004 |
| Acetone | Ethanol | Water | n-Butanol | Ethanol/Water | Water/n-Butanol | 009 |
| Acetone | Ethanol | Water | i-Butanol | Ethanol/Water | Water/i-Butanol | 009 |
| — | Acetone | n-Butyraldehyde | Water | n-Butyraldehyde/Water | — | 004 |
| — | Acetone | i-Butyraldehyde | Water | i-Butyraldehyde/Water | — | 004 |
| — | Methanol | Water | $C_5$+ Alcohol | Water/$C_5$+ Alcohol | — | 004 |
| — | Ethanol | Water | $C_5$+ Alcohol | Ethanol/Water | Water/$C_5$+ Alcohol | 009 |
| — | Methanol | Methacrolein | Water | Methanol/Methacrolein | Methacrolein/Water | 009 |
| — | Methanol | Water | Methyl Methacrylate | Water/Methyl Methacrylate | — | 004 |

The specific temperatures, pressures, and other operating conditions utilized within distillation systems as described herein may vary depending, at least in part, on the specific composition of the mixture being separated. Additionally, processes and systems as described herein may be used to separate mixtures that originate from any suitable type of process, including, but not limited to, chemical synthesis processes, biological processes such as fermentation, and the like.

The following examples are given to illustrate the invention and to enable any person skilled in the art to make and use the invention. It should be understood, however, that the invention is not to be limited to the specific conditions or details described in these examples. The patentable scope of the invention is defined by the claims, and may include other examples that occur to those skilled in the art.

EXAMPLES

Several distillation systems configured according to various embodiments of the present invention were simulated on a computer using ASPEN PLUS™ process simulation software commercially available from Aspen Technology, Inc. The simulations were performed using three RadFrac columns A, B, C and a decanter D as shown in the simulation process diagram provided in FIG. 7. Column A simulated a first stripping zone, Column B simulated the rectification zone, Column C simulated a second stripping zone, and Decanter D simulated a decantation zone. Although shown in FIG. 7 as including separate vessels, the simulation of a dividing wall column including each of the first and second stripping zones, a rectification zone, and a decantation zone would be simulated in a similar manner. Thus, the simulations described in the following Examples would be sufficient to simulate the performance and operation of a distillation system including a dividing wall distillation column or a distillation system including separate single distillation columns.

Figure 7:
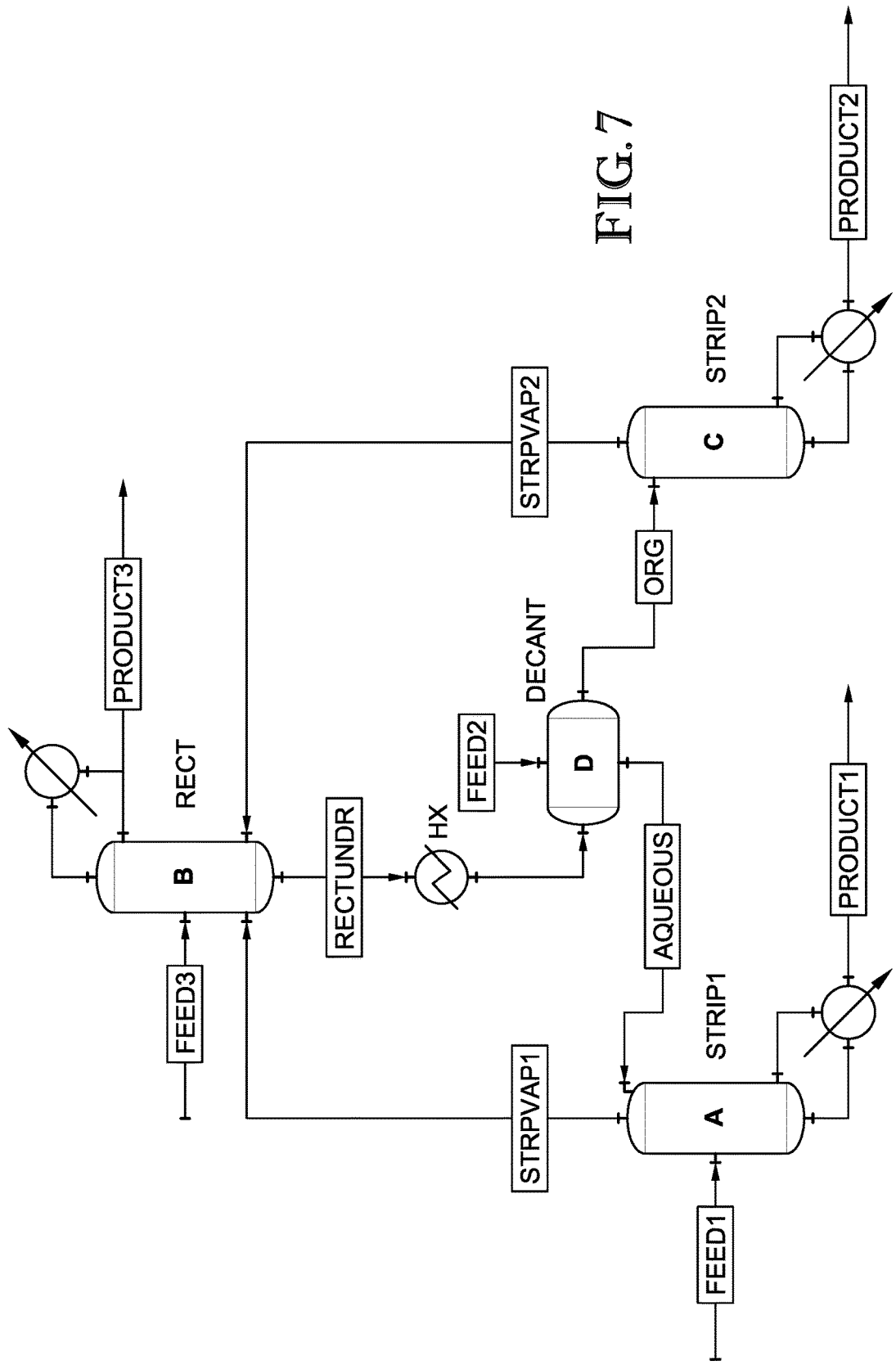
FIG. 7 is a schematic diagram representing the main components of the thermally integrated distillation system simulated in Examples 1-14.

Each simulation was performed using the system illustrated in FIG. 7, or a slight modification thereof. As shown in FIG. 7, Column A, labeled as STRIP1, represented the first stripping zone of the system, and Column C, labeled as STRIP2, represented the second stripping zone. Column B, labeled as RECT, represented the rectification zone, while the Decanter D, labeled DECANT, represented the decantation zone. The vapor stream withdrawn from the first stripping zone in Column A, labeled STRPVAP1, and the vapor stream withdrawn from the second stripping zone in Column C, labeled STRPVAP2, were introduced into the rectification zone in Column B. The overhead product withdrawn from the rectification zone in Column B, labeled PRODUCT3, was recovered as a product enriched in the light key component. The bottoms stream withdrawn from the rectification zone in Column B, labeled RECTUNDR, was cooled via heat exchanger HX to 25° C. before being introduced into the decantation zone in decanter D. Embodiments of the present invention may or may not include such a heat exchanger although it is simulated in the embodiments described with respect to the Examples.

For the simulations performed in the following Examples, the second liquid phase, labeled ORG, withdrawn from the decantation zone in decanter D was introduced into the second stripping zone in Column C, and the first liquid phase, labeled AQUEOUS, was introduced into the first stripping zone in Column A. Although labeled "AQUEOUS," this stream did not always contain water. For the simulations in the following Examples, the bottoms liquid stream withdrawn from the first stripping zone in Column A, labeled PRODUCT1, and the bottoms liquid stream withdrawn from the second stripping zone in Column C, labeled PRODUCT2, were product streams enriched in one of the heavy key and intermediate key components.

Each of the Examples provided below provides the results of a computer simulation performed with a different chemical mixture using the system shown in FIG. 7. For each simulation, the feed stream was introduced into one of the first stripping zone in Column A (shown as stream FEED1), the decantation zone in decanter D (shown as stream FEED2), and the rectification zone in Column B (shown as stream FEED3). Each simulation was performed at atmospheric pressure. Additional details for each simulation are provided in the Examples below.

Example 1

Figure 8:
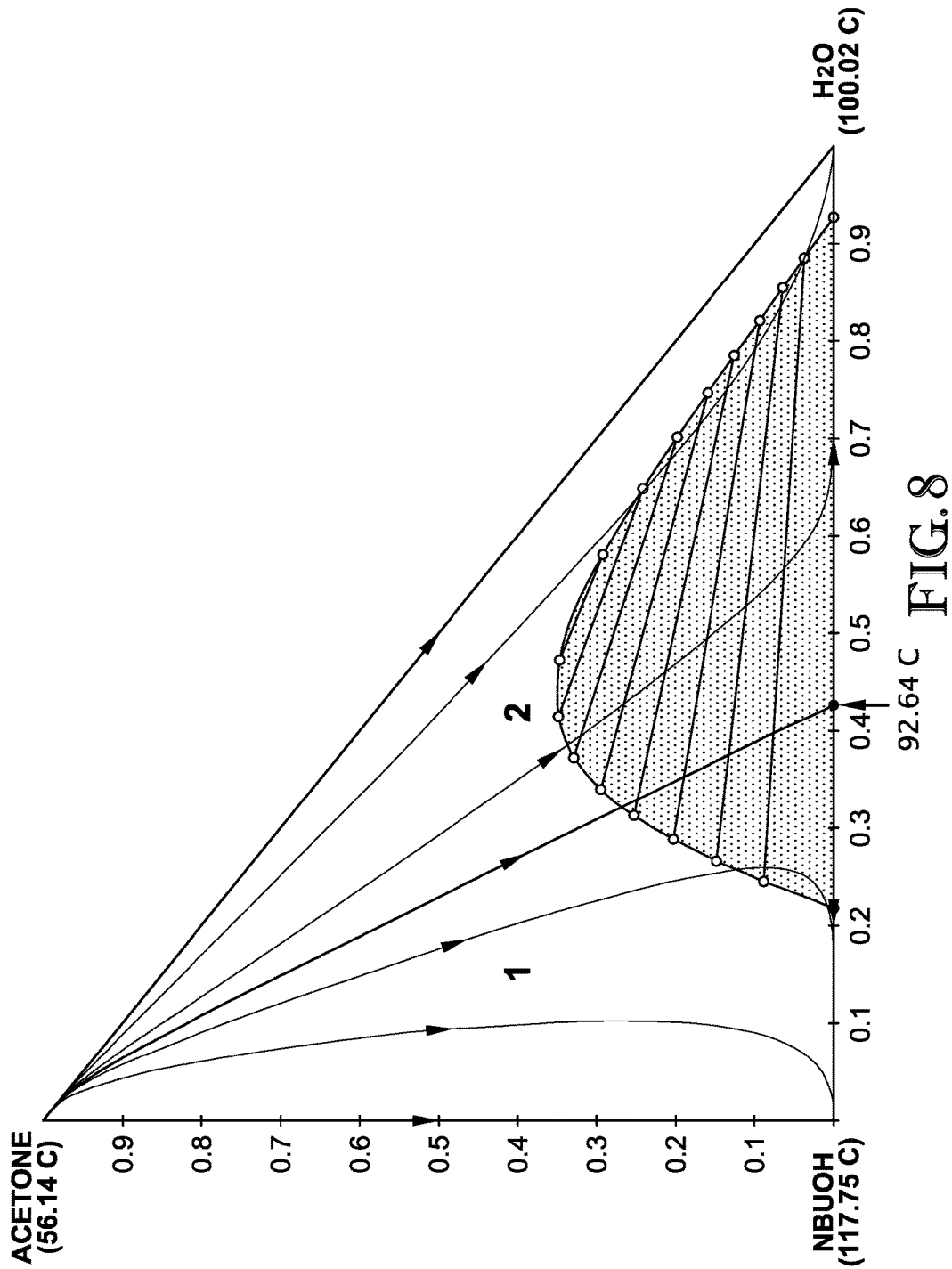
FIG. 8 is the Residue Curve Map for the acetone, water, and n-butanol system described in Examples 1-3.

A simulation as described above was performed for the distillation system shown in FIG. 7 for a feed stream including a mixture of acetone, water, and n-butanol. The mixture was characterized as a DRD #004 mixture and included a heterogeneous azeotrope between water, the intermediate key component (I), and n-butanol, the heavy key component (H), with a boundary between the I-H azeotrope and acetone, the light key component (L). The physical property method used to simulate the vapor-liquid behavior of the mixture for most of the system was NTRL and the decanter was simulated using UNIF-LL. The azeotropic information of the system is summarized in Table 2, below, and its residue curve map (RCM) is provided in FIG. 8.

TABLE 2

Physical Property Information for Acetone/Water/n-Butanol System at 1 atm

| Boiling Point | $x_{ij}$ (wt/wt) | | |
|---|---|---|---|
| (° C.) | Acetone | Water | n-Butanol |
| 56.1 | 1.00 | | |
| 92.6 | | 0.43 | 0.57 |
| 100.0 | | 1.00 | |
| 117.8 | | | 1.00 |

In this simulation (Simulation #1), the feed stream, which included 20 weight percent acetone, 60 weight percent water, and 20 weight percent n-Butanol, was sent directly into the decantation zone in Decanter D, as shown by the stream FEED2 in FIG. 7. This feed stream had a composition within the liquid-liquid region of the phase diagram shown in FIG. 8, and, consequently, was introduced directly into the decantation zone. Key input parameters for this simulation are provided in Table 3, below, and a summary of the simulation results are provided in Table 4.

TABLE 3

Summary of Key Input Parameters for Simulation #1 of Acetone/Water/n-Butanol System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.30 | — | — |
| Bottoms to Feed Weight Ratio | — | — | — | 0.79 | 0.20 |
| Physical Property Method | NRTL | UNIF-LL | NRTL | NRTL | NRTL |

TABLE 4

Summary of Simulation Results for Simulation #1 of Acetone/Water/n-Butanol System

| | Stream Composition (wt %) | | | |
|---|---|---|---|---|
| Component | FEED | PRODUCT1 | PRODUCT2 | PRODUCT3 |
| Acetone | 20.0 | <0.05 | <0.05 | 99.0 |
| Water | 60.0 | 98.8 | 0.4 | 1.0 |
| n-Butanol | 20.0 | 1.2 | 99.6 | <0.05 |

Example 2

A simulation was performed for a distillation system similar to the system shown in FIG. 7 for another feed stream including acetone, water, and n-butanol having a different composition than the feed stream simulated in Example 1. In this simulation (Simulation #2), the feed stream included 15 weight percent acetone, 20 weight percent water, and 65 weight percent n-butanol, and was located in Region 1 of the phase diagram shown in FIG. 8. As a result, the feed stream was simulated as being introduced into $10^{th}$ stage of the first stripping zone in Column A, as shown by the stream FEED1 in FIG. 7. Tables 5 and 6 summarize the key input parameters and simulation results for this simulation.

TABLE 5

Summary of Key Input Parameters for Simulation #2 of Acetone/Water/n-Butanol System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.20 | — | — |
| Bottoms to Feed Weight Ratio | — | — | — | 0.38 | 0.60 |
| Physical Property Method | NRTL | UNIF-LL | NRTL | NRTL | NRTL |

TABLE 6

Summary of Simulation Results for Simulation #2
of Acetone/Water/n-Butanol System

| | Stream Composition (wt %) | | | |
|---|---|---|---|---|
| Component | FEED | PRODUCT1 | PRODUCT2 | PRODUCT3 |
| Acetone | 15.0 | <0.05 | <0.05 | 99.0 |
| Water | 20.0 | <0.05 | 100.0 | 1.0 |
| n-Butanol | 65.0 | 100.0 | <0.05 | <0.05 |

Example 3

A simulation was performed for a distillation system similar to the system shown in FIG. 7 for yet another feed stream including acetone, water, and n-butanol having a different composition than the feed stream simulated in Examples 1 and 2. In this simulation (Simulation #3), the feed stream included 5 weight percent acetone, 90 weight percent water, and 5 weight percent n-butanol, and was located in Region 2 of the phase diagram of this ternary system shown in FIG. 8. Similarly to Example 2, the system was simulated so that the feed stream was introduced into the $10^{th}$ stage of the first stripping zone in Column A, as shown by the stream FEED1 in FIG. 7. Tables 7 and 8 summarize the key input parameters and simulation results for this simulation.

TABLE 7

Summary of Key Input Parameters for Simulation #3 of
Acetone/Water/n-Butanol System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.10 | — | — |
| Bottoms to Feed Weight Ratio | — | — | — | 0.70 | 0.40 |
| Physical Property Method | NRTL | UNIF-LL | NRTL | NRTL | NRTL |

TABLE 8

Summary of Simulation Results for Simulation #3
of Acetone/Water/n-Butanol System

| | Stream Composition (wt %) | | | |
|---|---|---|---|---|
| Component | FEED | PRODUCT1 | PRODUCT2 | PRODUCT3 |
| Acetone | 5.0 | <0.05 | <0.05 | 99.0 |
| Water | 90.0 | 100.0 | <0.05 | 1.0 |
| n-Butanol | 5.0 | <0.05 | 100.0 | <0.05 |

Example 4

Figure 9:
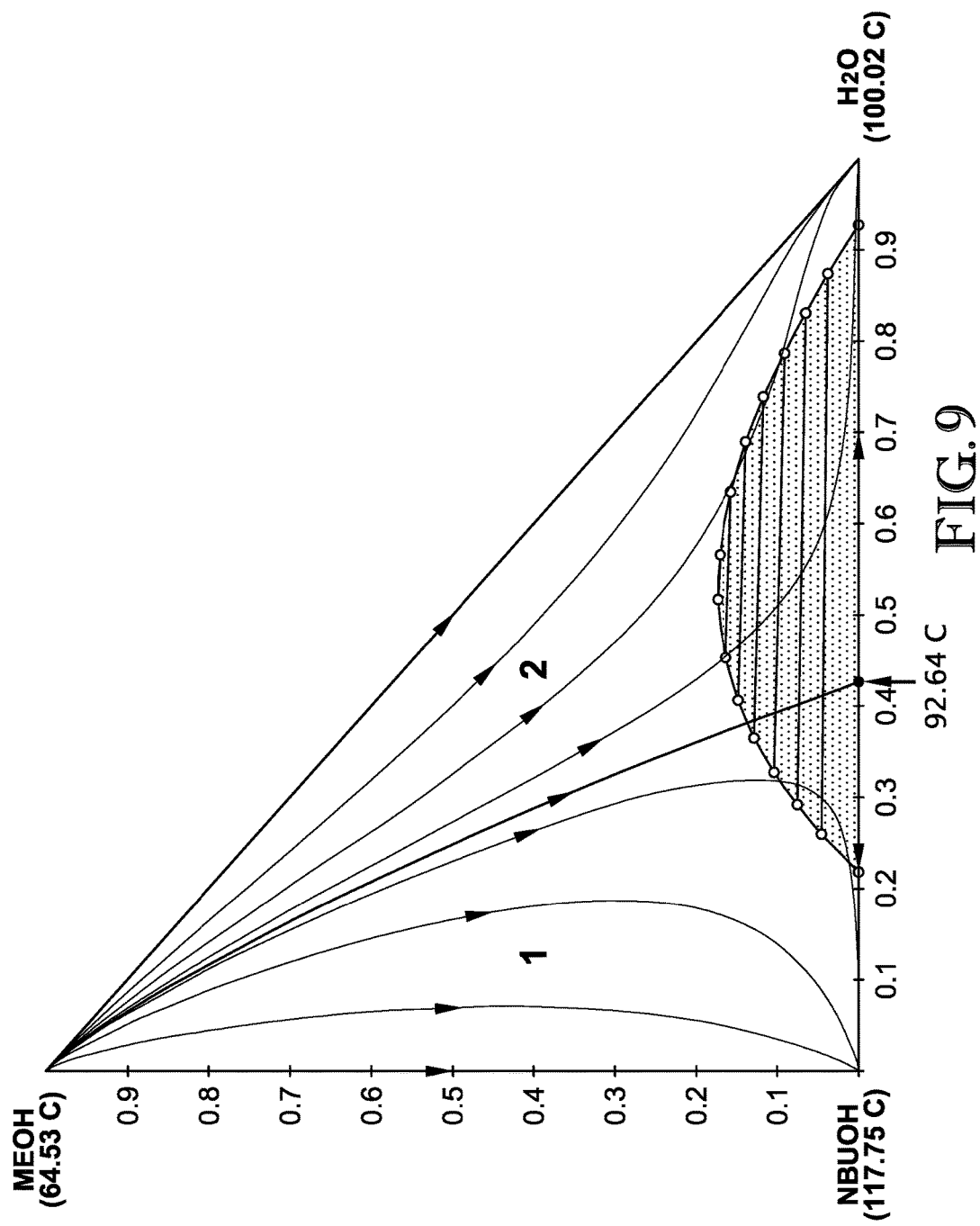
FIG. 9 is the Residue Curve Map for the methanol, water, and n-butanol system described in Examples 4-6.

A simulation was performed for a distillation system similar to the one shown in FIG. 7 for a feed stream including a mixture of methanol, water, and n-butanol. The mixture was characterized as a DRD #004 mixture and included a heterogeneous azeotrope between water, the intermediate key component (I), and n-butanol, the heavy key component (H), with a distillation boundary between the I-H azeotrope and methanol, the light key component (L). The physical property method used to simulate the vapor-liquid behavior of the mixture for most of the system was NTRL and the decanter was simulated using UNIF-LL. The azeotropic information of the system is summarized in Table 9, below, and the residue curve map (RCM) of this system is provided in FIG. 9.

TABLE 9

Physical Property Information for
Methanol/Water/n-Butanol System at 1 atm

| | $x_{ij}$ (wt/wt) | | |
|---|---|---|---|
| Boiling Point (° C.) | Methanol | Water | n-Butanol |
| 64.5 | 1.00 | | |
| 92.6 | | 0.43 | 0.57 |
| 100.0 | | 1.00 | |
| 117.8 | | | 1.00 |

In this simulation (Simulation #4), the feed stream, which included 10 weight percent methanol, 70 weight percent water, and 20 weight percent n-Butanol, was sent directly into the decantation zone in Decanter D. This feed stream had a composition within the liquid-liquid region of the phase diagram shown in FIG. 9, and, consequently, was introduced directly into the decantation zone in decanter D, as shown by stream FEED2 in FIG. 7. Key input parameters for this simulation are provided in Table 10, below, and a summary of the simulation results are provided in Table 11.

TABLE 10

Summary of Key Input Parameters for Simulation #4 of
Methanol/Water/n-Butanol System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.10 | — | — |
| Bottoms to Feed Weight Ratio | — | — | — | 0.70 | 0.22 |
| Physical Property Method | NRTL | UNIF-LL | NRTL | NRTL | NRTL |

TABLE 11

Summary of Simulation Results for Simulation #4
of Methanol/Water/n-Butanol System

| | Stream Composition (wt %) | | | |
|---|---|---|---|---|
| Component | FEED | PRODUCT1 | PRODUCT2 | PRODUCT3 |
| Methanol | 10.0 | <0.05 | <0.05 | 99.1 |
| Water | 70.0 | 100.0 | <0.05 | 0.8 |
| n-Butanol | 20.0 | <0.05 | 100.0 | <0.05 |

Example 5

Another simulation was performed for a distillation system similar to the system shown in FIG. 7 for a feed stream including methanol, water, and n-butanol having a different composition than the feed stream simulated in Example 4. In this simulation (Simulation #5), the feed stream included 15 weight percent methanol, 30 weight percent water, and 55 weight percent n-butanol, and was located in Region 1 of the phase diagram shown in FIG. 9. As a result, the feed stream was simulated as being introduced into $10^{th}$ stage of the first stripping zone in Column A, as shown by stream FEED1 in FIG. 7. Tables 12 and 13 summarize the key input parameters and simulation results for this simulation.

TABLE 12

Summary of Key Input Parameters for Simulation #5 of Methanol/Water/n-Butanol System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.10 | — | — |
| Bottoms to Feed Weight Ratio | — | — | — | 0.27 | 0.80 |
| Physical Property Method | NRTL | UNIF-LL | NRTL | NRTL | NRTL |

TABLE 13

Summary of Simulation Results for Simulation #5 of Methanol/Water/n-Butanol System

| | Stream Composition (wt %) | | | |
|---|---|---|---|---|
| Component | FEED | PRODUCT1 | PRODUCT2 | PRODUCT3 |
| Methanol | 15.0 | <0.05 | <0.05 | 100.0 |
| Water | 30.0 | 0.1 | 100.0 | <0.05 |
| n-Butanol | 55.0 | 99.9 | <0.05 | <0.05 |

Example 6

Another simulation was performed for a distillation system similar to the system shown in FIG. 7 with a feed stream including methanol, water, and n-butanol having a different composition than the feed streams simulated in Examples 4 and 5. In this simulation (Simulation #6), the feed stream included 10 weight percent methanol, 75 weight percent water, and 15 weight percent n-butanol, and was located in Region 2 of the phase diagram of this ternary system shown in FIG. 9. Similarly to Example 5, the system was simulated was similar to the system depicted in FIG. 7, except the feed stream was introduced into $10^{th}$ stage of the first stripping zone in Column A, as shown by stream FEED1 in FIG. 7. Tables 14 and 15 summarize the key input parameters and results for this simulation.

TABLE 14

Summary of Key Input Parameters for Simulation #6 of Methanol/Water/n-Butanol System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.08 | — | — |
| Bottoms to Feed Weight Ratio | — | — | — | 0.43 | 0.36 |
| Physical Property Method | NRTL | UNIF-LL | NRTL | NRTL | NRTL |

TABLE 15

Summary of Simulation Results for Simulation #6 of Methanol/Water/n-Butanol System

| | Stream Composition (wt %) | | | |
|---|---|---|---|---|
| Component | FEED | PRODUCT1 | PRODUCT2 | PRODUCT3 |
| Methanol | 10.0 | <0.05 | <0.05 | 99.2 |
| Water | 75.0 | 100.0 | <0.05 | 0.8 |
| n-Butanol | 15.0 | <0.05 | 100.0 | <0.05 |

Example 7

Figure 10:
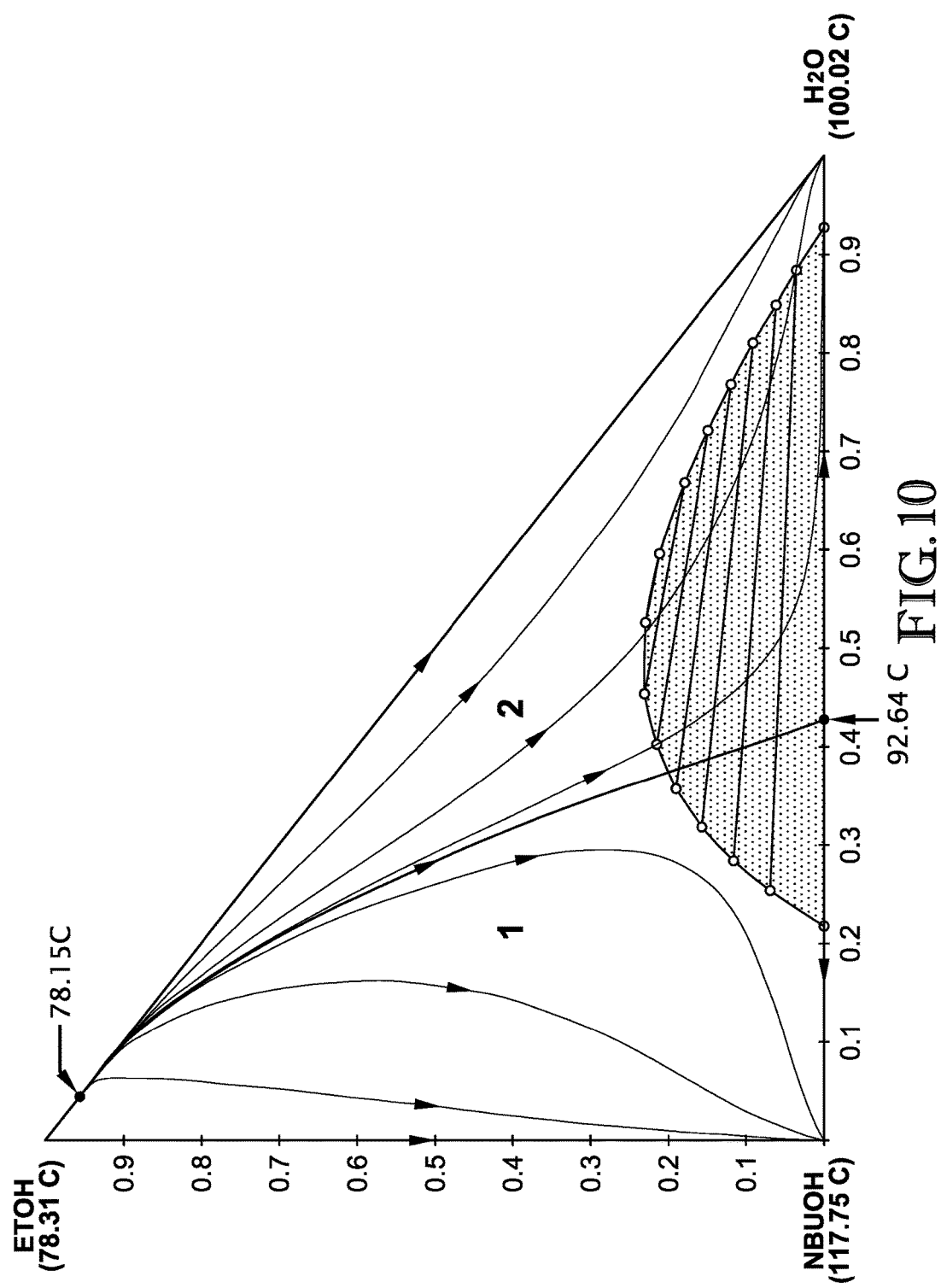
FIG. 10 is the Residue Curve Map for the systems including ethanol, water, and n-butanol as described in Examples 7-10.

A simulation was performed for a distillation system similar to the one shown in FIG. 7 for a feed stream including a mixture of ethanol, water, and n-butanol. The mixture was characterized as a DRD #009 mixture and included a heterogeneous azeotrope between water, the intermediate key component (I), and n-butanol, the heavy key component (H), and a homogeneous azeotrope between ethanol, the light key component (L), and water (I) with a boundary between the water/n-butanol (I-H) azeotrope and the ethanol/water (L-I) azeotrope. The physical property method used to simulate the vapor-liquid behavior of the mixture for most of the system was NTRL, and the decanter was simulated using UNIF-LL. The azeotropic information of the system is summarized in Table 16, below, and the residue curve map (RCM) of this system is provided in FIG. 10. Because this mixture further included a L-I azeotrope, the purity of the overhead product from the rectification zone in Column B was limited by this azeotrope, and, as a result, the PRODUCT3 stream could not be distilled to form pure ethanol.

TABLE 16

Physical Property Information for Ethanol/Water/n-Butanol System at 1 atm

| | $x_{ij}$ (wt/wt) | | |
|---|---|---|---|
| Boiling Point (° C.) | Ethanol | Water | n-Butanol |
| 78.2 | 0.96 | 0.04 | |
| 78.3 | 1.00 | | |
| 92.6 | | 0.43 | 0.57 |
| 100.0 | | 1.00 | |
| 117.8 | | | 1.00 |

In this simulation (Simulation #7), the feed stream, which included 20 weight percent ethanol, 60 weight percent water, and 20 weight percent n-butanol, was sent directly into the decantation zone in Decanter D. This feed stream had a composition within the liquid-liquid region of the phase diagram shown in FIG. 10, and, consequently, was introduced directly into the decantation zone in Decanter D, as shown by the stream FEED2 in FIG. 7. Key input parameters for this simulation are provided in Table 17, below, and a summary of the simulation results are provided in Table 18.

TABLE 17

Summary of Key Input Parameters for Simulation #7 of Ethanol/Water/n-Butanol System

| Property | Value | | | | |
|---|---|---|---|---|---|
| | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.11 | — | — |
| Bottoms to Feed Weight Ratio | — | — | — | 0.73 | 0.10 |
| Physical Property Method | NRTL | UNIF-LL | NRTL | NRTL | NRTL |

TABLE 18

Summary of Simulation Results for Simulation #7 of Ethanol/Water/n-Butanol System

| Component | Stream Composition (wt %) | | | |
|---|---|---|---|---|
| | FEED | PRODUCT1 | PRODUCT2 | PRODUCT3 |
| Ethanol | 20.0 | <0.05 | <0.05 | 92.8 |
| Water | 60.0 | 100.0 | <0.05 | 7.2 |
| n-Butanol | 20.0 | <0.05 | 100.0 | <0.05 |

Example 8

Another simulation was performed for a distillation system similar to the system shown in FIG. 7 for a feed stream including ethanol, water, and n-butanol having a different composition than the feed stream simulated in Example 7. In this simulation (Simulation #8), the feed stream included 15 weight percent ethanol, 20 weight percent water, and 65 weight percent n-butanol, and was located in Region 1 of the phase diagram shown in FIG. 10. As a result, the feed stream was simulated as being introduced into $10^{th}$ stage of the first stripping zone in Column A, as shown by the stream FEED1 in FIG. 7. Tables 19 and 20 summarize the key input parameters and simulation results for this simulation.

TABLE 19

Summary of Key Input Parameters for Simulation #8 of Ethanol/Water/n-Butanol System

| Property | Value | | | | |
|---|---|---|---|---|---|
| | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.12 | — | — |
| Bottoms to Feed Weight Ratio | — | — | — | 0.33 | 0.79 |

TABLE 19-continued

Summary of Key Input Parameters for Simulation #8 of Ethanol/Water/n-Butanol System

| Property | Value | | | | |
|---|---|---|---|---|---|
| | HX | DECANT | RECT | STRIP1 | STRIP2 |
| Physical Property Method | NRTL | UNIF-LL | NRTL | NRTL | NRTL |

TABLE 20

Summary of Simulation Results for Simulation #8 of Ethanol/Water/n-Butanol System

| Component | Stream Composition (wt %) | | | |
|---|---|---|---|---|
| | FEED | PRODUCT1 | PRODUCT2 | PRODUCT3 |
| Ethanol | 15 | 0 | 0 | 93.6 |
| Water | 20 | 0 | 100 | 6.4 |
| n-Butanol | 65 | 100 | 0 | 0 |

Example 9

Another simulation was performed for a distillation system similar to the system shown in FIG. 7 with a feed stream including ethanol, water, and n-butanol having a different composition than the feed streams simulated in Examples 7 and 8. In this simulation (Simulation #9), the feed stream included 5 weight percent ethanol, 90 weight percent water, and 5 weight percent n-butanol, and was located in Region 2 of the phase diagram of this ternary system shown in FIG. 10. Similarly to Example 8, the system was simulated was similar to the system depicted in FIG. 7, except the feed stream was introduced into $10^{th}$ stage of the first stripping zone in Column A, as shown by the stream FEED1 of FIG. 7. Tables 21 and 22 summarize the key input parameters and results for this simulation.

TABLE 21

Summary of Key Input Parameters for Simulation #9 of Ethanol/Water/n-Butanol System

| Property | Value | | | | |
|---|---|---|---|---|---|
| | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.10 | — | — |
| Bottoms to Feed Weight Ratio | — | — | — | 0.76 | 0.17 |
| Physical Property Method | NRTL | UNIF-LL | NRTL | NRTL | NRTL |

TABLE 22

Summary of Simulation Results for Simulation #9 of Ethanol/Water/n-Butanol System

| Component | Stream Composition (wt %) | | | |
|---|---|---|---|---|
| | FEED | PRODUCT1 | PRODUCT2 | PRODUCT3 |
| Ethanol | 5.0 | <0.05 | <0.05 | 94.6 |
| Water | 90.0 | 100.0 | 0.4 | 5.4 |
| n-Butanol | 5.0 | <0.05 | 99.6 | <0.05 |

Example 10

A simulation was performed for a distillation system similar to the one shown in FIG. 7 for a feed stream that included a mixture of acetone, ethanol, water, and n-butanol. Because such a mixture does not form any ternary or higher azeotropes, the simulation is similar to the ethanol/water/n-butanol mixtures simulated previously in Examples 7-9. Because acetone is less volatile than ethanol, the overhead from the rectification zone in Column B was enriched in acetone and ethanol, and the bottoms streams withdrawn from the first stripping zone in Column A and the second stripping zone in Column C were enriched in n-butanol and water, respectively. The physical property method used to simulate the vapor-liquid behavior of the mixture for most of the system was NTRL, and the decanter was simulated using UNIF-LL. The azeotropic information of the system is summarized in Table 23, below.

TABLE 23

Physical Property Information for Acetone/Ethanol/Water/n-Butanol System at 1 atm

| Boiling Point | $x_{ij}$ (wt/wt) | | | |
|---|---|---|---|---|
| (° C.) | Acetone | Ethanol | Water | n-Butanol |
| 56.1 | 1.0 | | | |
| 78.2 | | 0.96 | 0.04 | |
| 78.3 | | 1.00 | | |
| 92.6 | | | 0.43 | 0.57 |
| 100.0 | | | 1.00 | |
| 117.8 | | | | 1.00 |

In this simulation (Simulation #10), the feed stream, which included 5 weight percent acetone, 5 weight percent ethanol, 85 weight percent water, and 5 weight percent n-butanol, was fed onto the 10$^{th}$ stage of the first stripping zone in Column A, as shown by stream FEED1 in FIG. 7. Key input parameters for this simulation are provided in Table 24, below, and a summary of the simulation results are provided in Table 25.

TABLE 24

Summary of Key Input Parameters for Simulation #10 of Acetone/Ethanol/Water/n-Butanol System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.13 | — | — |
| Bottoms to Feed Weight Ratio | — | — | — | 0.76 | 0.08 |
| Physical Property Method | NRTL | UNIF-LL | NRTL | NRTL | NRTL |

TABLE 25

Summary of Simulation Results for Simulation #10 of Acetone/Ethanol/Water/n-Butanol System

| | Stream Composition (wt %) | | | |
|---|---|---|---|---|
| Component | FEED | PRODUCT1 | PRODUCT2 | PRODUCT3 |
| Acetone | 5.0 | <0.05 | <0.05 | 46.0 |
| Ethanol | 5.0 | <0.05 | <0.05 | 46.0 |
| Water | 85.0 | 100.0 | <0.05 | 7.5 |
| n-Butanol | 5.0 | <0.05 | 100.0 | 0.4 |

Example 11

Figure 11:
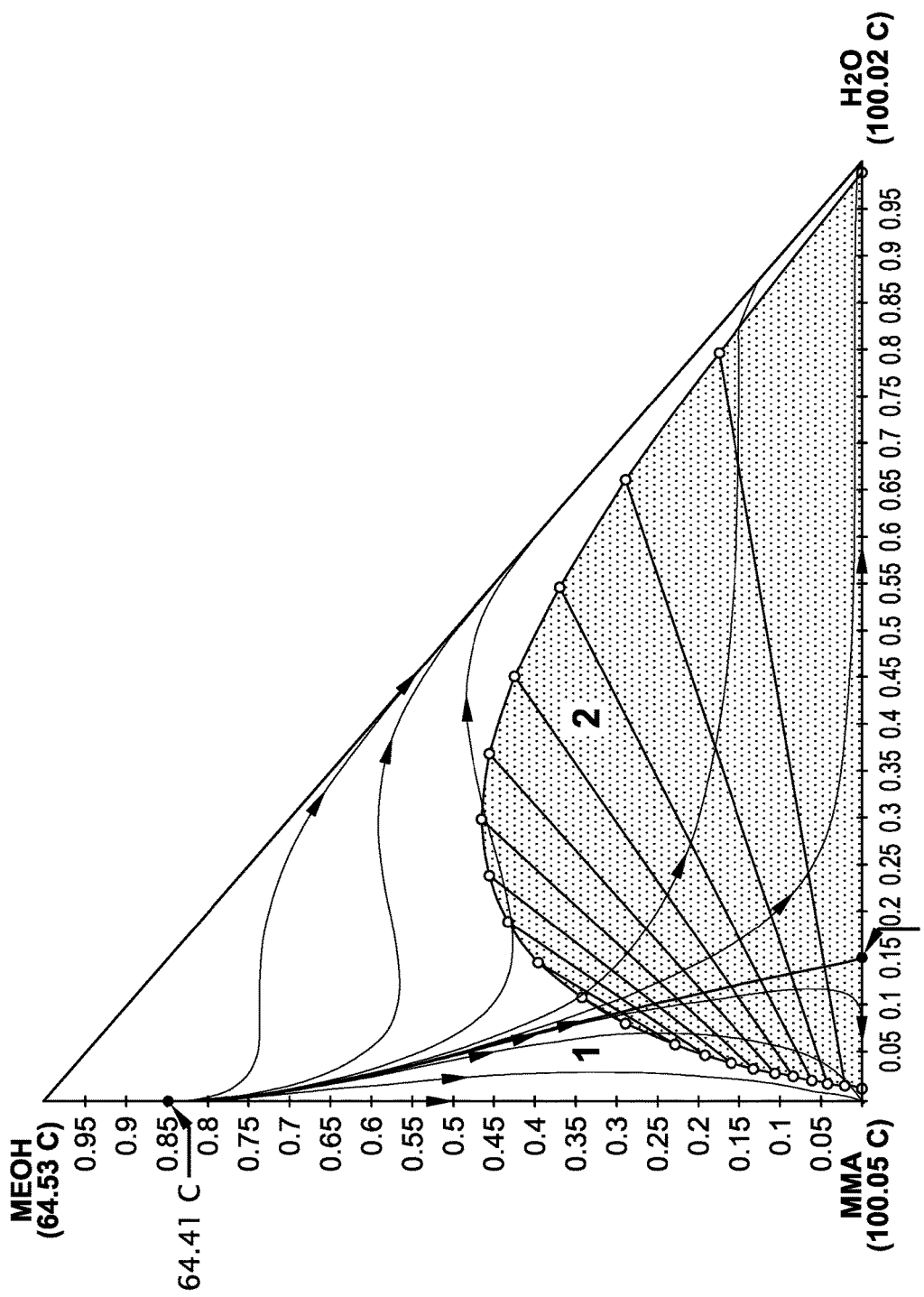
FIG. 11 is the Residue Curve Map for the systems including methanol, water, and methyl methacrylate as described in Examples 11-14.

A simulation was performed for a distillation system similar to the one shown in FIG. 7 for a feed stream including a mixture of methanol, water, and methyl methacrylate (MMA). The mixture was characterized as a DRD #006 mixture and included a heterogeneous azeotrope between water, the intermediate key component (I), and MMA, the heavy key component (H), and a homogeneous azeotrope between methanol, the light key component (L), and MMA (H) with a boundary between the water/MMA (I-H) azeotrope and the methanol/MMA (L-H) azeotrope. The physical property method used to simulate the vapor-liquid behavior of the entire system was UNIQUAC. The azeotropic information of the system is summarized in Table 26, below, and the residue curve map (RCM) of this system is provided in FIG. 11.

TABLE 26

Physical Property Information for Methanol/Water/MMA System at 1 atm

| Boiling Point | $x_{ij}$ (wt/wt) | | |
|---|---|---|---|
| (° C.) | Methanol | Water | MMA |
| 64.4 | 0.85 | | 0.15 |
| 64.5 | 1.00 | | |
| 81.6 | | 0.15 | 0.85 |
| 100.0 | | 1.00 | |
| 100.1 | | | 1.00 |

In this simulation (Simulation #11), the feed stream, which included 25 weight percent methanol, 50 weight percent water, and 25 weight percent MMA, was sent directly into the decantation zone in Decanter D, as shown by the stream FEED2 in FIG. 7. This feed stream had a composition within the liquid-liquid region of the phase diagram shown in FIG. 11. Key input parameters for this simulation are provided in Table 27, below, and a summary of the simulation results are provided in Table 28.

TABLE 27

Summary of Key Input Parameters for Simulation #11 of Methanol/Water/MMA System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.12 | — | — |
| Bottoms to Feed Weight Ratio | — | — | — | 0.22 | 0.18 |

TABLE 27-continued

Summary of Key Input Parameters for Simulation
11 of Methanol/Water/MMA System

| | Value | | | | |
|---|---|---|---|---|---|
| Property | HX | DECANT | RECT | STRIP1 | STRIP2 |
| Physical Property Method | | | UNIQUAC | | |

TABLE 28

Summary of Simulation Results for Simulation
11 of Methanol/Water/MMA

| | Stream Composition (wt %) | | | |
|---|---|---|---|---|
| Component | FEED | PRODUCT1 | PRODUCT2 | PRODUCT3 |
| Methanol | 25.0 | <0.05 | <0.05 | 79.5 |
| Water | 50.0 | 100.0 | <0.05 | <0.05 |
| MMA | 25.0 | <0.05 | 100.0 | 20.4 |

Example 12

Another simulation was performed for a distillation system similar to the system shown in FIG. 7 for a feed stream including methanol, water, and MMA having a different composition than the feed stream simulated in Example 11. In this simulation (Simulation #12), the feed stream included 10 weight percent methanol, 10 weight percent water, and 80 weight percent MMA, and was located in Region 1 of the phase diagram shown in FIG. 11. As a result, the feed stream was simulated as being introduced into $10^{th}$ stage of the first stripping zone in Column A, as shown by the stream FEED1 in FIG. 7. Tables 29 and 30 summarize the key input parameters and simulation results for this simulation.

TABLE 29

Summary of Key Input Parameters for Simulation
12 of Methanol/Water/MMA System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.09 | — | — |
| Bottoms to Feed Weight Ratio | — | — | — | 0.47 | 0.16 |
| Physical Property Method | | | UNIQUAC | | |

TABLE 30

Summary of Simulation Results for Simulation
12 of Methanol/Water/MMA System

| | Stream Composition (wt %) | | | |
|---|---|---|---|---|
| Component | FEED | PRODUCT1 | PRODUCT2 | PRODUCT3 |
| Methanol | 10.0 | <0.05 | <0.05 | 79.5 |
| Water | 10.0 | <0.05 | 100.0 | 0.1 |
| MMA | 80.0 | 100.0 | <0.05 | 20.5 |

Example 13

Another simulation was performed for a distillation system similar to the system shown in FIG. 7 with a feed stream including methanol, water, and MMA having a different composition than the feed streams simulated previously. In this simulation (Simulation #13), the feed stream included 5 weight percent methanol, 60 weight percent water, and 35 weight percent MMA, and was located in Region 2 of the phase diagram of this ternary system shown in FIG. 11. Similarly to Example 12, the system was simulated was similar to the system depicted in FIG. 7, except the feed stream was introduced into $10^{th}$ stage of the first stripping zone in Column A, as shown by the stream FEED1 in FIG. 7. Tables 31 and 32 summarize the key input parameters and results for this simulation.

TABLE 31

Summary of Key Input Parameters for Simulation
13 of Methanol/Water/MMA System

| | Value | | | | |
|---|---|---|---|---|---|
| Property | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.05 | — | — |
| Bottoms to Feed Weight Ratio | — | — | — | 0.48 | 0.32 |
| Physical Property Method | | | UNIQUAC | | |

TABLE 32

Summary of Simulation Results for Simulation
13 of Methanol/Water/MMA System

| | Stream Composition (wt %) | | | |
|---|---|---|---|---|
| Component | FEED | PRODUCT1 | PRODUCT2 | PRODUCT3 |
| Methanol | 5.0 | <0.05 | <0.05 | 81.2 |
| Water | 60.0 | 100.0 | <0.05 | <0.05 |
| MMA | 35.0 | <0.05 | 100.0 | 18.8 |

Example 14

Another simulation was performed for a distillation system similar to the system shown in FIG. 7 with a feed stream including methanol, water, and MMA having a different composition than the feed streams simulated previously. In this simulation (Simulation #14), the feed stream included 38 weight percent methanol, 9 weight percent water, and 53 weight percent MMA. In this case, with the feed being rich in the light key component (methanol), but not located within the liquid-liquid region of the phase diagram shown in FIG. 11, the feed was introduced into the rectification zone in Column B, as shown by stream FEED3 in FIG. 7. As a result, a significant portion of the light key component was removed, thereby providing a rectification liquid having a composition within the liquid-liquid region of the phase diagram. Tables 33 and 34 summarize the key input parameters and results for this simulation.

TABLE 33

Summary of Key Input Parameters for Simulation #14 of Methanol/Water/MMA System

| Property | Value | | | | |
|---|---|---|---|---|---|
| | HX | DECANT | RECT | STRIP1 | STRIP2 |
| Temperature, ° C. | 25 | 25 | — | — | — |
| Pressure, atm | 1 | 1 | 1 | 1 | 1 |
| No. of Stages | — | — | 20 | 20 | 20 |
| Distillate to Feed Weight Ratio | — | — | 0.20 | — | — |
| Bottoms to Feed Weight Ratio | — | — | — | 0.07 | 0.70 |
| Physical Property Method | | | UNIQUAC | | |

TABLE 34

Summary of Simulation Results for Simulation #14 of Methanol/Water/MMA System

| | Stream Composition (wt %) | | | |
|---|---|---|---|---|
| Component | FEED | PRODUCT1 | PRODUCT2 | PRODUCT3 |
| Methanol | 38.0 | <0.05 | <0.05 | 79.8 |
| Water | 9.0 | 100.0 | <0.05 | <0.05 |
| MMA | 53.0 | <0.05 | 100.0 | 20.1 |

DEFINITIONS

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Equivalents to determine and assess the reasonably fair scope of the present invention as pertains to any apparatus not materially departing from but outside the literal scope of the invention as set forth in the following claims.

The invention claimed is:

1. A method for separating a ternary mixture comprising a light key component, a heavy key component, and at least one intermediate key component, wherein said mixture has a distillation boundary on a distillation region diagram that intersects a heterogeneous, minimum boiling binary azeotrope between said intermediate key component and said heavy key component that has a higher boiling point than the light key component, said method comprising:
   (a) introducing a feed stream comprising said mixture into a thermally integrated distillation system comprising a rectification zone, a first stripping zone, a second stripping zone, and a decantation zone;
   (b) withdrawing first and second overhead vapor streams from said first and said second stripping zones respectively;
   (c) introducing said first and said second overhead vapor streams into said rectification zone;
   (d) withdrawing a rectification liquid stream from said rectification zone;
   (e) introducing said rectification liquid stream into said decantation zone;
   (f) separating said rectification liquid stream in said decantation zone into a first liquid phase enriched in said heavy key component and a second liquid phase enriched in said intermediate key component, wherein said first and said second liquid phases have compositions that are in different distillation regions of said distillation region diagram;
   (g) introducing a first liquid stream comprising at least a portion of said first liquid phase into one of said first stripping zone and said second stripping zone;
   (h) introducing a second liquid stream comprising at least a portion of said second liquid phase into the other of said first stripping zone and said second stripping zone;
   (i) recovering a first bottoms product stream enriched in said heavy key component from said first stripping zone;
   (j) recovering a second bottoms product stream enriched in said intermediate key component from said second stripping zone; and
   (k) recovering a first overhead product stream enriched in said light key component from said rectification zone.

2. The method of claim 1, wherein said introducing of step (a) includes feeding said feed stream into said first stripping zone, said second stripping zone, said rectification zone, and/or said decantation zone.

3. The method of claim 1, wherein said introducing of step (a) includes feeding said feed stream into said first stripping zone, and wherein said feed stream has a composition in a distillation region of said distillation region diagram that contains a heavy key component vertex.

4. The method of claim 1, wherein said introducing of step (a) includes feeding said feed stream into said second stripping zone and wherein said feed stream has a composition in a distillation region of said distillation region diagram that contains an intermediate key component vertex.

5. The method of claim 1, wherein said introducing of step (a) includes feeding said feed stream into said rectification zone, and wherein said feed stream has a higher concentration of said light key component than of said intermediate key component or said heavy key component.

6. The method of claim 1, wherein said introducing of step (a) includes feeding said feed stream into said decantation zone, wherein said separating of step (f) further comprises separating said feed stream to form said first liquid phase and said second liquid phase.

7. The method of claim 1, wherein said light key component and said intermediate key component form a minimum boiling binary azeotrope.

8. The method of claim 1, wherein said light key component and said heavy key component forms a minimum boiling binary azeotrope.

9. The method of claim 1, wherein said distillation boundary intersects a light key component vertex of said distillation region diagram.

10. The method of claim 1, wherein said mixture further comprises one or more components having a higher volatility than said light key component, one or more components having a lower volatility than said heavy key component, and/or one or more additional intermediate components.

11. The method of claim 1, wherein said thermally integrated distillation system comprises a dividing wall distillation column, wherein said rectification zone is located within an upper portion of an internal volume of said dividing wall distillation column, wherein said first stripping zone and said second stripping zone are located within a lower portion of said internal volume of said dividing wall distillation column, and wherein said first and said second stripping zones are separated by a dividing wall.

12. The method of claim 11, wherein said decantation zone is located within said internal volume of said dividing wall distillation column between said rectification zone and said first and said second stripping zones.

13. The method of claim 11, wherein said decantation zone is located outside said internal volume of said dividing wall distillation column.

14. The method of claim 1, wherein said thermally integrated distillation system comprises a first distillation column, a second distillation column, and a third distillation column, wherein said rectification zone, said first stripping zone, and said second stripping zone are respectively defined within said first, said second, and said third distillation columns, and wherein said decantation zone is located outside each of said first, said second, and said third distillation columns.

15. The method of claim 1, wherein said mixture comprises at least one of the following groups of components selected from the group consisting of (i) through (x) below:
   (i) n-butylamine/water/n-butanol/dibutylamine/tributylamine;
   (ii) n-butyraldehyde/water/2-ethylhexenal;
   (iii) propionaldehyde/water/2-methylpentenal;
   (iv) propionaldehyde/n-butyraldehyde/water;
   (v) acetone/water/n-butanol;
   (vi) acetone/ethanol/water/n-butanol;
   (vii) methanol/methacrolein/water;
   (viii) methanol/water/methyl methacrylate;
   (ix) acetone/water/ketone; and
   (x) methanol/water/xylene/dimethyterephthalate.

* * * * *